(12) United States Patent
Banerjee et al.

(10) Patent No.: US 11,591,564 B2
(45) Date of Patent: Feb. 28, 2023

(54) PEPTIDE CONJUGATED HYDROGEL SUBSTRATE FOR THE MAINTENANCE AND EXPANSION OF HUMAN PLURIPOTENT STEM CELLS

(71) Applicant: University of Pittsburgh—Of the Commonwealth System of Higher Education, Pittsburgh, PA (US)

(72) Inventors: Ipsita Banerjee, Pittsburgh, PA (US); Prashant Kumta, Pittsburgh, PA (US); Thomas Richardson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/842,005

(22) Filed: Dec. 14, 2017

(65) Prior Publication Data
US 2018/0171286 A1 Jun. 21, 2018

Related U.S. Application Data

(60) Provisional application No. 62/550,906, filed on Aug. 28, 2017, provisional application No. 62/435,128, filed on Dec. 16, 2016.

(51) Int. Cl.
| | |
|---|---|
| *C12N 5/00* | (2006.01) |
| *C07K 14/00* | (2006.01) |
| *C07K 7/04* | (2006.01) |
| *C07K 14/705* | (2006.01) |
| *C12N 5/0735* | (2010.01) |
| *C07K 17/10* | (2006.01) |

(52) U.S. Cl.
CPC .............. *C12N 5/0068* (2013.01); *C07K 7/04* (2013.01); *C07K 14/00* (2013.01); *C07K 14/705* (2013.01); *C07K 17/10* (2013.01); *C12N 5/0012* (2013.01); *C12N 5/0018* (2013.01); *C12N 5/0606* (2013.01); *C12N 2513/00* (2013.01); *C12N 2533/74* (2013.01); *C12N 2537/10* (2013.01)

(58) Field of Classification Search
CPC .............. C12N 5/00018; C12N 5/0068; C12N 5/0018; C12N 5/068; C07K 14/00; C07K 14/705
See application file for complete search history.

(56) References Cited

U.S. PATENT DOCUMENTS

| | | | | |
|---|---|---|---|---|
| 6,642,363 | B1 * | 11/2003 | Mooney | A61K 35/34 536/124 |
| 2004/0006011 | A1 | 1/2004 | Gour et al. | |
| 2005/0222037 | A1 * | 10/2005 | Blaschuk | C07K 14/705 514/44 R |
| 2009/0311765 | A1 | 12/2009 | Maguire et al. | |
| 2010/0239540 | A1 | 9/2010 | Brinchmann et al. | |
| 2015/0252148 | A1 * | 9/2015 | Lee | C12N 5/0068 435/395 |
| 2016/0377600 | A1 * | 12/2016 | Cho | C08J 3/28 525/199 |
| 2018/0346902 | A1 * | 12/2018 | Jansen | C12N 11/04 |

FOREIGN PATENT DOCUMENTS

| | | |
|---|---|---|
| WO | 0234880 A2 | 5/2002 |
| WO | 2006122147 A2 | 11/2006 |
| WO | 2008157324 A2 | 12/2008 |

OTHER PUBLICATIONS

Abbasalizadeh et al., "Bioprocess Development for Mass Production of Size-Controlled Human Pluripotent Stem Cell Aggregates in Stirred Suspension Bioreactor", Tissue Engineering: Part C, 2012, pp. 831-851, vol. 18, No. 11.
Amit et al., "Dynamic suspension culture for scalable expansion of undifferentiated human pluripotent stem cells", Nature Protocols, 2011, pp. 572-579, vol. 6, Issue 5.
Bardy et al., "Microcarrier Suspension Cultures for High-Density Expansion and Differentiation of Human Pluripotent Stem Cells to Neural Progenitor Cells", Tissue Engineering: Part C, 2013, pp. 166-180, vol. 19, Issue 2.
Bian et al., "Hydrogels that mimic developmentally relevant matrix and N-cadherin interations enhance MSC chondrogenesis", Proceedings of the National Academy of Sciences of the United States of America, 2013, pp. 10117-10122, vol. 110, Issue 25.
Boggon et al., "C-cadherin Ectodomain Structure and Implications for Cell Adhesion Mechanisms", Science Magazine, 2002, pp. 1308-1313, vol. 296.
Braam et al., "Recombinant Vitronectin Is a Functionally Defined Substrate That Supports Human Embryonic Stem Cell Self-Renewal via Alpha V Beta 5 Integrin", Stem Cells, 2008, pp. 2257-2265, vol. 26.
Chappuis-Flament et al., "Multiple cadherin extracellular repeats mediate homophilic binding and adhesion", The Journal of Cell Biology, 2001, pp. 231-243, vol. 154, Issue 1.
Chen et al., "Critical microcarrier properties affecting the expansion of undifferentiated human embryonic stem cells", Stem Cell Research, 2011, pp. 97-111, vol. 7.
Chen et al., "E-Cadherin-Mediated Cell-Cell Contact Is Critical for Induced Pluripotent Stem Cell Generation", Stem Cells, 2010, pp. 1315-1325, vol. 28.

(Continued)

*Primary Examiner* — Marcia S Noble
(74) *Attorney, Agent, or Firm* — The Webb Law Firm

(57) ABSTRACT

Compositions useful for propagation of pluripotent stem cells are provided. The compositions comprise a polysaccharide hydrogel linked to a peptide fragment of the extracellular domain of epithelial cadherin. Methods of making the composition, and culturing pluripotent stem cells also are provided.

12 Claims, 14 Drawing Sheets
Specification includes a Sequence Listing.

(56) References Cited

OTHER PUBLICATIONS

Chen et al., "Scalable GMP compliant suspension culture system for human ES cells", Stem Cell Research, 2012, pp. 388-402, vol. 8.

Deng et al., "Long-term self-renewal of human pluripotent stem cells on peptide-decorated poly(OEGMA-co-HEMA) brushes under fully defined conditions", Acta Biomaterialia, 2013, pp. 8840-8850, vol. 9.

Disclosure for grant on Jun. 16, 2015, https://www.nsf.gov/awardsearch/showAward?AWD_ID=1547618.

Disclosure to NPR, http://wesa.fm/post/pitt-scientist-receivces-grant-mass-produce-stem-cells#stream/0.

Disclosure to Pitt Chronicle, https://www.chronicle.pitt.edu/story/pitt-researchers-are-working-mass-produce-stem-cells.

Feng et al., "Rho Kinase (ROCK) Inhibitors and Their Therapeutic Potential", Journal of Medicinal Chemistry, 2016, pp. 2269-2300, vol. 59.

Haque et al., "The effect of recombinant E-cadherin substratum on the differentiation of endoderm-derived hepatocyte-like cells from embryonic stem cells", Biomaterials, 2011, pp. 2032-2042, vol. 32.

Higuchi et al., "Long-term xeno-free culture of human pluripotent stem cells on hydrogels with optimal elasticity", Scientific Reports, 2015, vol. 5, Article 18136.

Jenkins et al., "Human pluripotent stem cell-derived products: advances towards robust, scalable and cost-effective manufacturing strategies", Biotechnology Journal, 2015, pp. 83-95, vol. 10.

Kehoe et al., "Scalable Stirred-Suspension Bioreactor Culture of Human Pluripotent Stem Cells", Tissue Engineering Part A, 2010, pp. 405-421, vol. 16, Issue 2.

Kiptoo et al., "Enhancement of Drug Absorption through the Blood-Brain Barrier and Inhibition of Intercellular Tight Junction Resealing by E-Cadherin Peptides", Molecular Pharmaceutics, 2011, pp. 239-249, vol. 8, Issue 1.

Kobayashi et al., "Inhibition of E-Cadherin-Mediated Homotypic Adhesion of Caco-2 Cells: A Novel Evaluation Assay for Peptide Activities in Modulating Cell-Cell Adhesion", The Journal of Pharmacology and Experimental Therapies, 2006, pp. 309-316, vol. 317, Issue 1.

Krawetz et al., Large-Scale Expansion of Pluripotent Human Embryonic Stem Cells in Stirred-Suspension Bioreactors, Tissue Engineering: Part C, 2010 pp. 573-582, vol. 16, Issue 4.

Kurosawa, "Application of Rho-associated protein kinase (ROCK) inhibitor to human pluripotent stem cells", Journal of Bioscience and Bioengineering, 2012, pp. 577-581, vol. 114, Issue 6.

Li et al., "Role of E-cadherin and other cell adhesion molecules in survival and differentiation of human pluripotent stem cells", Cell Adhesion & Migration, 2012, pp. 59-70, vol. 6, Issue 1.

Ludwig et al., "Feeder-independent culture of human embryonic stem cells", Nature Methods, 2006, pp. 637-646, vol. 3, Issue 8.

Makagiansar et al., "Improving the Selectivity of HAV-Peptides in Modulating E-Cadherin-E-Cadherin Interactions in the Intercellular Junction of MDCK Cell Monolayers", Pharmaceutical Research, 2001, pp. 446-453, vol. 18, Issue 4.

Melkoumian et al., "Synthetic peptide-acrylate surfaces for long-term self-renewal and cardiomyocyte differentiation of human embryonic stem cells", Nature Biotechnology, 2010, pp. 606-610, vol. 28.

Nagaoka et al., "Culture of human pluripotent stem cells using completely defined conditions on a recombinant E-cadherin substratum", BMC Developmental Biology, 2010, pp. 1-12, vol. 10, Issue 60.

Noe et al., "Inhibition of adhesion and induction of epithelial cell invasion by HAV-containing E-cadherin-specific peptides", Journal of Cell Science, 1999, pp. 127-135, vol. 112.

Olmer et al., "Long term expansion of undifferentiated human iPS and ES cells in suspension culture using a defined medium", Stem Cell Research, 2010, pp. 51-64, vol. 5.

Olmer et al., "Suspension Culture of Human Pluripotent Stem Cells in Controlled, Stirred Bioreactors", Tissue Engineering: Part C, 2012, pp. 772-784, vol. 18, Issue 10.

Parisini et al., "The crystal structure of human E-cadherin domains 1 and 2, and comparison with other cadherins in the context of adhesion mechanism", Journal of Molecular Biology, 2007, pp. 401-411, vol. 373, Issue 2.

Renaud-Young et al., "In the First Extracellular Domain of E-cadherin, Heterophilic Interactions, but Not the Conserved His-Ala-Val Motif, Are Required for Adhesion", The Journal of Biological Chemistry, 2002, pp. 39609-39616, vol. 277, Issue 42.

Rodin et al., "Clonal culturing of human embryonic stem cells on laminin-521/E-cadherin matrix in defined and xeno-free environment", Nature Communications, 2014, vol. 5, Article 3195.

Rowley et al., "Alginate hydrogels as synthetic extracellular matrix materials", Biomaterials, 1999 pp. 45-53, vol. 20.

Schulz et al., "A Scalable System for Production of Functional Pancreatic Progenitors from Human Embryonic Stem Cells", PLoS One, 2012, e37004, vol. 7, Issue 5.

Serra et al., "Improving expansion of pluripotent human embryonic stem cells in perfused bioreactors through oxygen control", Journal of Biotechnology, 2010, pp. 208-215, vol. 148, Issue 4.

Sinaga et al., "Increasing Paracellular Porosity by E-Cadherin Peptides: Discovery of Bulge and Groove Regions in the EC1-Domain of E-Cadherin", Pharmaceutical Research, 2002, pp. 1170-1179, vol. 19, Issue 8.

Singh et al., "Up-scaling single cell-inoculated suspension culture of human embryonic stem cells", Stem Cell Research, 2010, pp. 165-179, vol. 4.

Ting et al., "An intermittent rocking platform for integrated expansion and differentiation of human pluripotent stem cells to cardiomyocytes in suspended microcarrier cultures", Stem Cell Research, 2014, pp. 202-213, vol. 13.

Wang et al., "Efficient and scalable expansion of human pluripotent stem cells under clinically compliant settings: a view in 2013", Analysis of Biomedical Engineering, 2014, pp. 1357-1372, vol. 42, Issue 7.

Watanabe et al., "A Rock inhibitor permits survival of dissociated human embryonic stem cells", Nature Biotechnology, 2007, pp. 681-686, vol. 25, Issue 6.

Zhu et al., "Hydrogels functionalized with N-cadherin mimetic peptide enhance osteogenesis of hMSCs by emulating the osteogenic niche", Biomaterials, 2016, pp. 44-52, vol. 77.

Zhu et al., "Human pluripotent stem cells: an emerging model in developmental biology", Development, 2013, pp. 705-717, vol. 140.

Zweigerdt et al., "Scalable expansion of human pluripotent stem cells in suspension culture", Nature Protocols, 2011, pp. 689-700, vol. 6, Issue 5.

\* cited by examiner

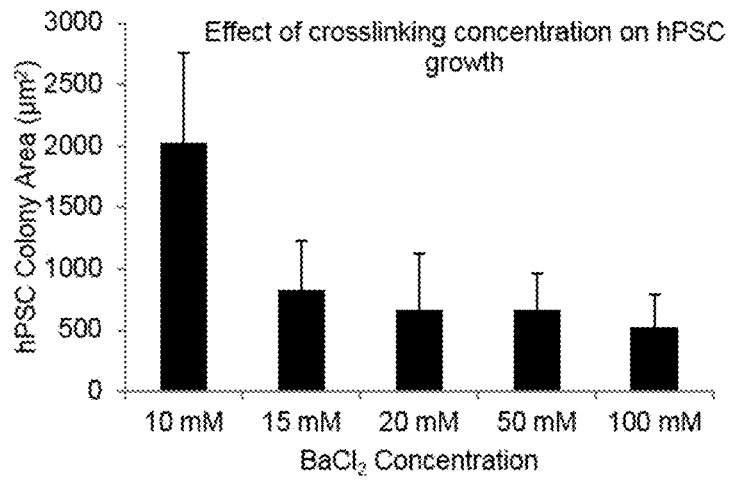

Fig. 4

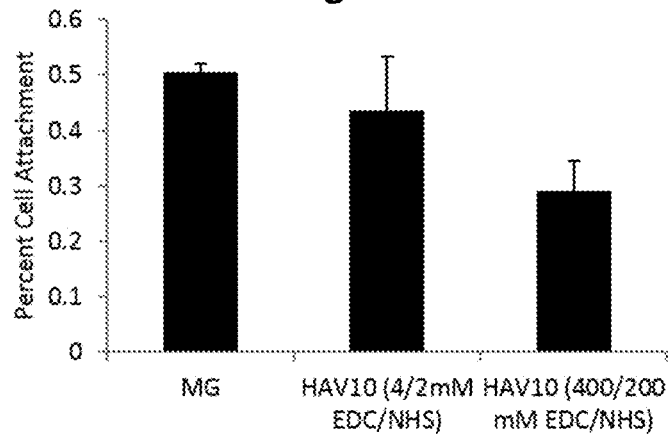

Fig. 5

MGPWSRSLSALLLLLQVSSWLCQEPEPCHPGFDAESYTFTVPRRHLERGRVLGRVNFEDC
TGRQRTAYFSLDTRFKVGTDGVITVKRPLRFHNPQIHFLVYAWDSTYRKFSTKVTLNTVG
HHHRPPPHQASVSGIQAELLTFPNSSPGLRRQKRDWVIPPISCPENEKGPFPKNLVQIKS
NKDKEGKVFYSITGQGADTPPVGVFIIERETGWLKVTEPLDRERIATYTLFSHAVSSNGN
AVEDPMEILITVTDQNDNKPEFTQEVFKGSVMEGALPGTSVMEVTATDADDDVNTYNAAI
AYTILSQDPELPDKNMFTINRNTGVISVVTTGLDRESFPTYTLVVQAADLQGEGLSTTAT
AVITVTDTNDNPPIFNPTTYKGQVPENEANVVITTLKVTDADAPNTPAWEAVYTILNDDG
GQFVVTTNPVNNDGILKTAKGLDFEAKQQYILHVAVTNVVPFEVSLTTSTATVTVDVLDV
NEAPIFVPPEKRVEVSEDFGVGQEITSYTAQEPDTFMEQKITYRIWRDTANWLEINPDTG
AISTRAELDREDFEHVKNSTYTALIIATDNGSPVATGTGTLLLILSDVNDNAPIPEPRTI
FFCERNPKPQVINIIDADLPPNTSPFTAELTHGASANWTIQYNDPTQESIILKPKMALEV
GDYKINLKLMDNQNKDQVTTLEVSVCDCEGAAGVCRKAQPVEAGLQIPAILGILGGILAL
LILILLLLFLRRRAVVKEPLLPPEDDTRDNVYYYDEEGGGEEDQDFDLSQLHRGLDARP
EVTRNDVAPTLMSVPRYLPRPANPDEIGNFIDENLKAADTDPTAPPYDSLLVFDYEGSGS
EAASLSSLNSSESDKDQDYDYLNEWGNRFKKLADMYGGGEDD

Fig. 6

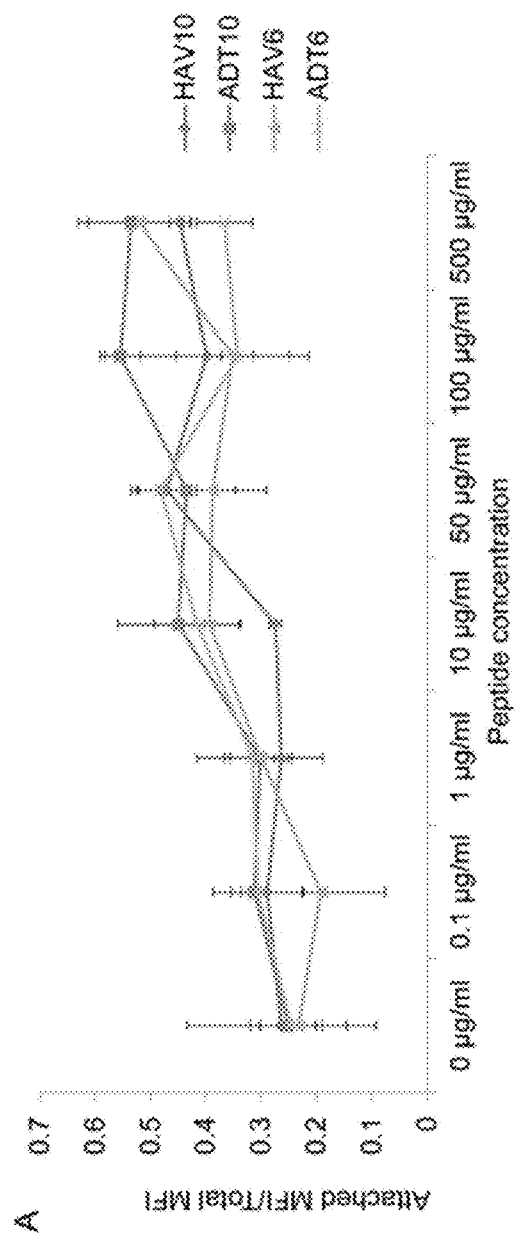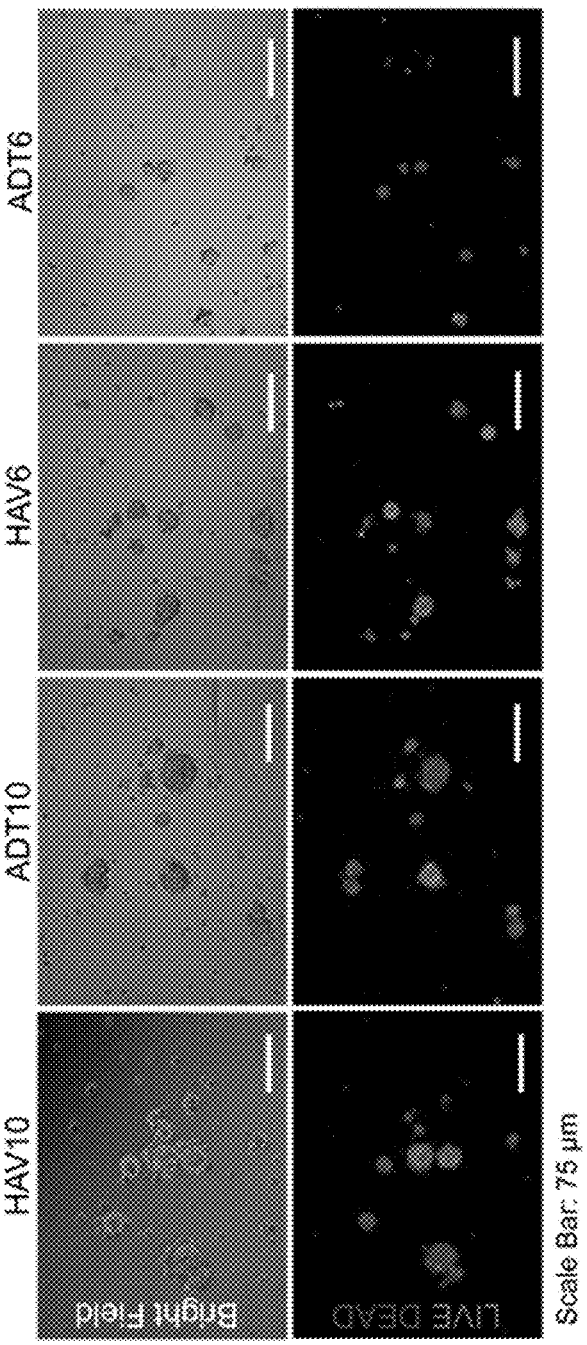
Fig. 9

PEPTIDE CONJUGATED HYDROGEL SUBSTRATE FOR THE MAINTENANCE AND EXPANSION OF HUMAN PLURIPOTENT STEM CELLS

CROSS REFERENCE TO RELATED APPLICATIONS

This application claims the benefit of United States Provisional Patent Application Nos. 62/550,906 filed Aug. 28, 2017, and 62/435,128 filed Dec. 16, 2016, each of which is incorporated herein by reference in its entirety.

STATEMENT REGARDING FEDERAL FUNDING

This invention was made with government support under Grant No. CBET1547618 awarded by the National Science Foundation. The government has certain rights in the invention.

REFERENCE TO A SEQUENCING LISTING

The Sequence Listing associated with this application is filed in electronic format via EFS-Web and is hereby incorporated by reference into the specification in its entirety. The name of the text file containing the Sequence Listing is 1708890ST25.txt. The size of the text file is 8,863 bytes, and the text file was created on Dec. 6, 2017.

The path to clinical translation of laboratory scale scientific advances in hPSCs includes implementation of reproducible, scalable culture and differentiation protocols. Criterion for hPSC scale up platforms includes the maintenance of high viability and proliferation without compromising pluripotency and differentiation potency. However, hPSC survival and proliferation requires cell-cell contact, failing which results in dissociation induced apoptosis. This requirement significantly restricts options for scalable cultures, which has inspired novel avenues for hPSC scale-up.

With maintenance of cell-cell contact being of such importance to hPSC survival, these cells are commonly cultured and propagated as colonies on adherent 2D substrates. The most commonly used method employs propagation on tissue culture plastic coated with Matrigel, an animal derived ECM protein cocktail. However, being animal derived and expensive, this limits the scalability for use in cellular therapy applications. Suspension culture systems, on the other hand, are intrinsically better suited for scalable cultures because of geometric scalability. Current methods of suspension cultures of hPSCs include microcarrier culture and cell aggregate culture. Microcarrier culture offers the unique advantage of scaling up adherent hPSCs. While uniquely suited for hPSCs, this platform possesses a high propensity for undesirable cell clustering, along with problematic separation of cells from the carrier. Currently the most promising scalable platform is aggregate-based suspension culture of single cell inoculation with ROCK inhibition, which supports long-term cell survival in an undifferentiated state. Challenges with the current suspension cultures are (i) maintaining homogeneity of cell aggregates and (ii) accounting for the uncontrolled shear stress on the surface of aggregates. Specifically, the response of hPSCs to shear stress varies with cell lines, hence reducing the versatility of the platform. Overcoming these shortcomings would be significant in establishing a robust and controlled stem cell biomanufacturing platform.

With ongoing clinical trials with human pluripotent stem cells, there is a need for rapid and controlled expansion of the cells to meet clinical demand. Clonal expansion (generating millions of cells from a single cell) is the ultimate goal in mass production of these cells, but hPSCs do not survive as single cells. Methods and compositions useful in propagating hPSCs are desirable.

SUMMARY

According to one aspect, a composition for use in propagating pluripotent stem cells from single cells is provided. The composition comprises a biocompatible hydrogel, optionally a synthetic or naturally derived (natural) polysaccharide hydrogel, linked to a polypeptide comprising a cell-binding sequence of an epithelial cadherin, optionally human epithelial cadherin, extracellular domain.

In another aspect, a method of making a composition supportive of pluripotent cell expansion, is provided. The method comprises conjugating (covalently attaching) a polypeptide comprising a cell-binding sequence of an epithelial cadherin, such as human epithelial cadherin, extracellular domain to a biocompatible hydrogel, optionally to a synthetic or naturally derived polysaccharide hydrogel.

In another aspect, a method of preparing a cell growth composition is provided. The method comprises: conjugating a polypeptide comprising a cell-binding sequence of an epithelial cadherin, such as human epithelial cadherin, extracellular domain with a polysaccharide, such as a carboxylated polysaccharide, to produce a polypeptide-conjugated polysaccharide; mixing pluripotent stem cells with the polypeptide-conjugated polysaccharide; and optionally culturing the cells in cell culture medium, such as stem cell medium, optionally exposing the cells in culture to a ROCK inhibitor, such as Y-27632, within the first 1, 2, 3, or 4, days of culture, thereby expanding the cells, wherein when the cells are pluripotent, the cells retain their pluripotency.

In yet another aspect, a device is provided. The device comprises a substrate, a first intermediate layer over at least a portion of the substrate comprising a first anionic polysaccharide layer over at least a portion of the substrate and a cationic polyamine layer over at least a portion of the anionic layer, and a second anionic polysaccharide layer over at least a portion of the cationic polyamine layer, wherein the polysaccharide of the first and/or second anionic polysaccharide layer is linked to a polypeptide comprising a cell-binding sequence of an E-cadherin extracellular domain.

In another aspect, a method of preparing a multi-layered composition for use in propagating pluripotent stem cells from single cells is provided, comprising, e.g., in order: forming an intermediate layer by forming a first anionic layer over a substrate by depositing a biocompatible natural or synthetic anionic polysaccharide over at least a portion of the substrate and forming a first cationic layer by depositing a polyamine, such as poly(allylamine), such as a poly(allylamine hydrochloride) over at least a portion of the first anionic layer; and forming a second anionic layer over the substrate by depositing a biocompatible natural or synthetic anionic polysaccharide over at least a portion of the first cationic layer, wherein the polysaccharide of either or both of the intermediate layer or the second anionic layer is covalently linked to a polypeptide comprising a cell-binding sequence of an E-cadherin extracellular domain prior to or after depositing the polysaccharide over the substrate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a graph showing the effect of Barium Chloride (BaCl2) concentration on growth of hPSCs encapsulated in alginate beads.

FIG. 5 is a graph showing the effect of EDC/NHS concentration on hPSC cell attachment and viability.

FIG. 6 provides an exemplary amino acid sequence for one isoform of human e-cadherin (UniProtKB-P12830 (CADH1_HUMAN), (SEQ ID NO: 1)).

FIG. 9. Cell attachment to e-cadherin peptide modified alginate. (A) Percent cell attachment after 1 day, determined by normalized attached cell MFI by total cell MFI. Cell attachment was analyzed for each peptide, conjugated at 0-500 µg/ml. (B) Representative LIVE/DEAD images for cell attached to each peptide modified hydrogel, conjugated with 50 µg/ml.

DETAILED DESCRIPTION

Figure 1:
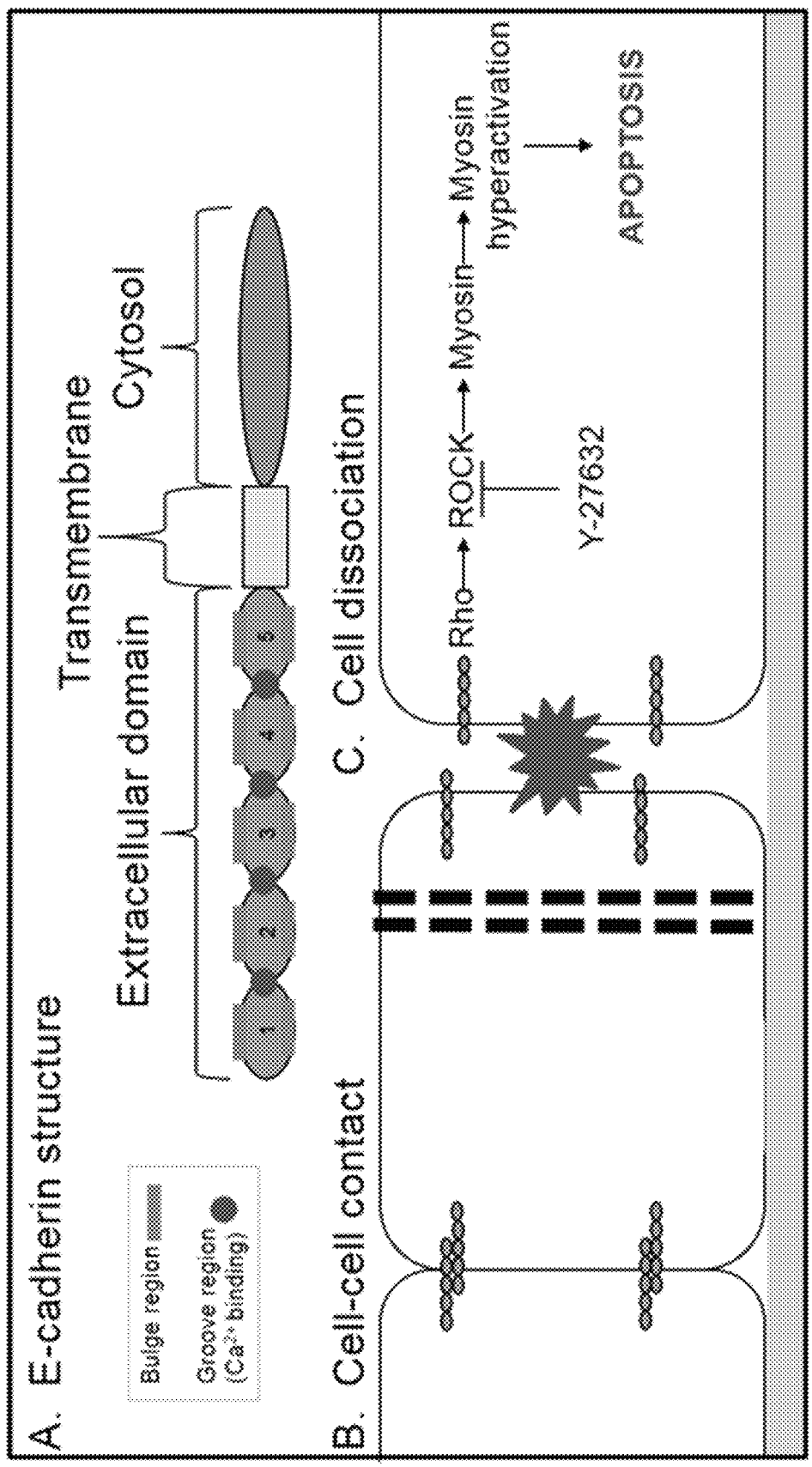
FIG. 1 is a schematic diagram showing the E-cadherin junction between hPSCs.
Figure 2:
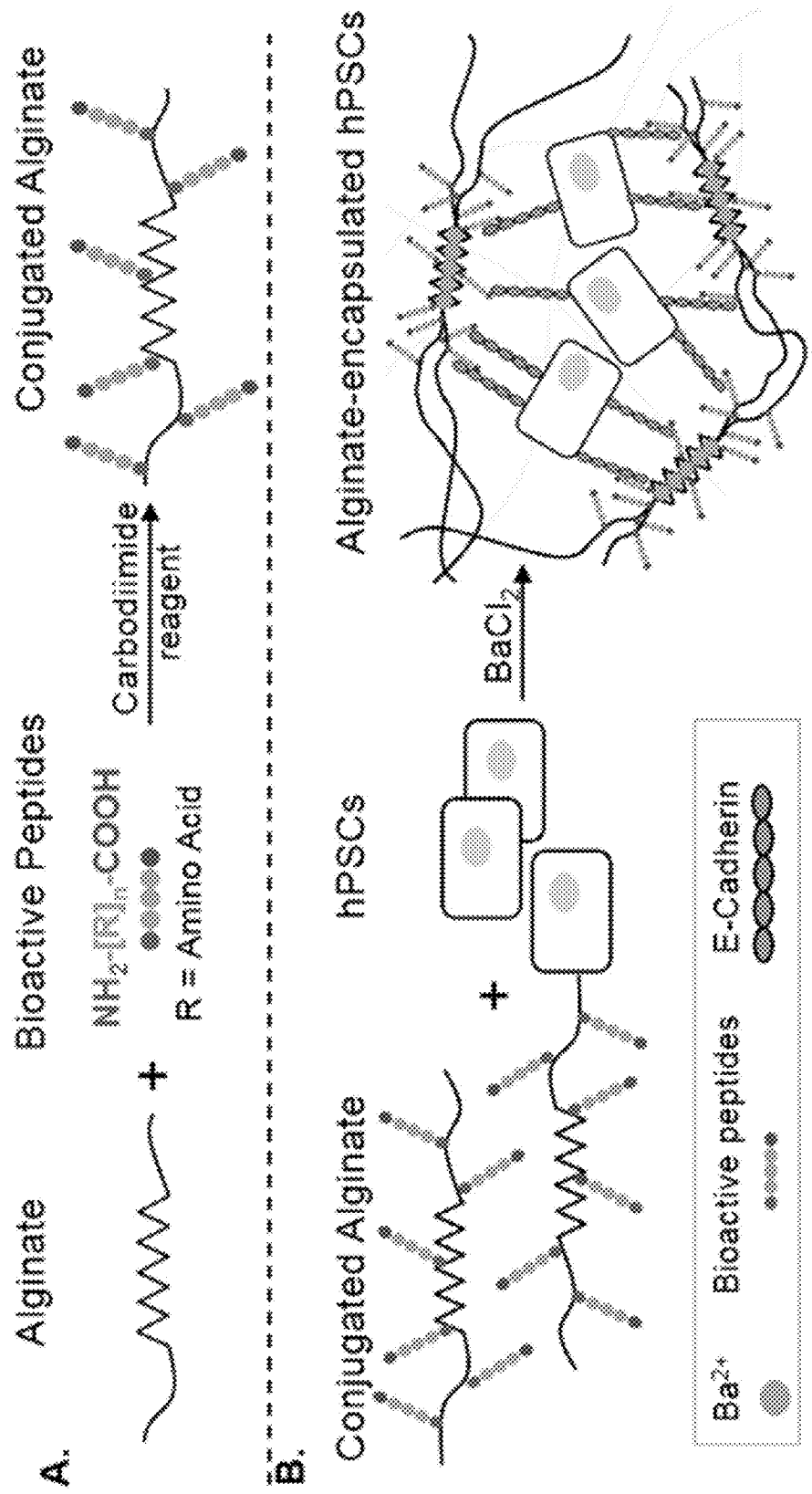
FIG. 2 is a schematic diagram showing HAV10 conjugation to alginate and encapsulation of hPSCs.
Figure 3:
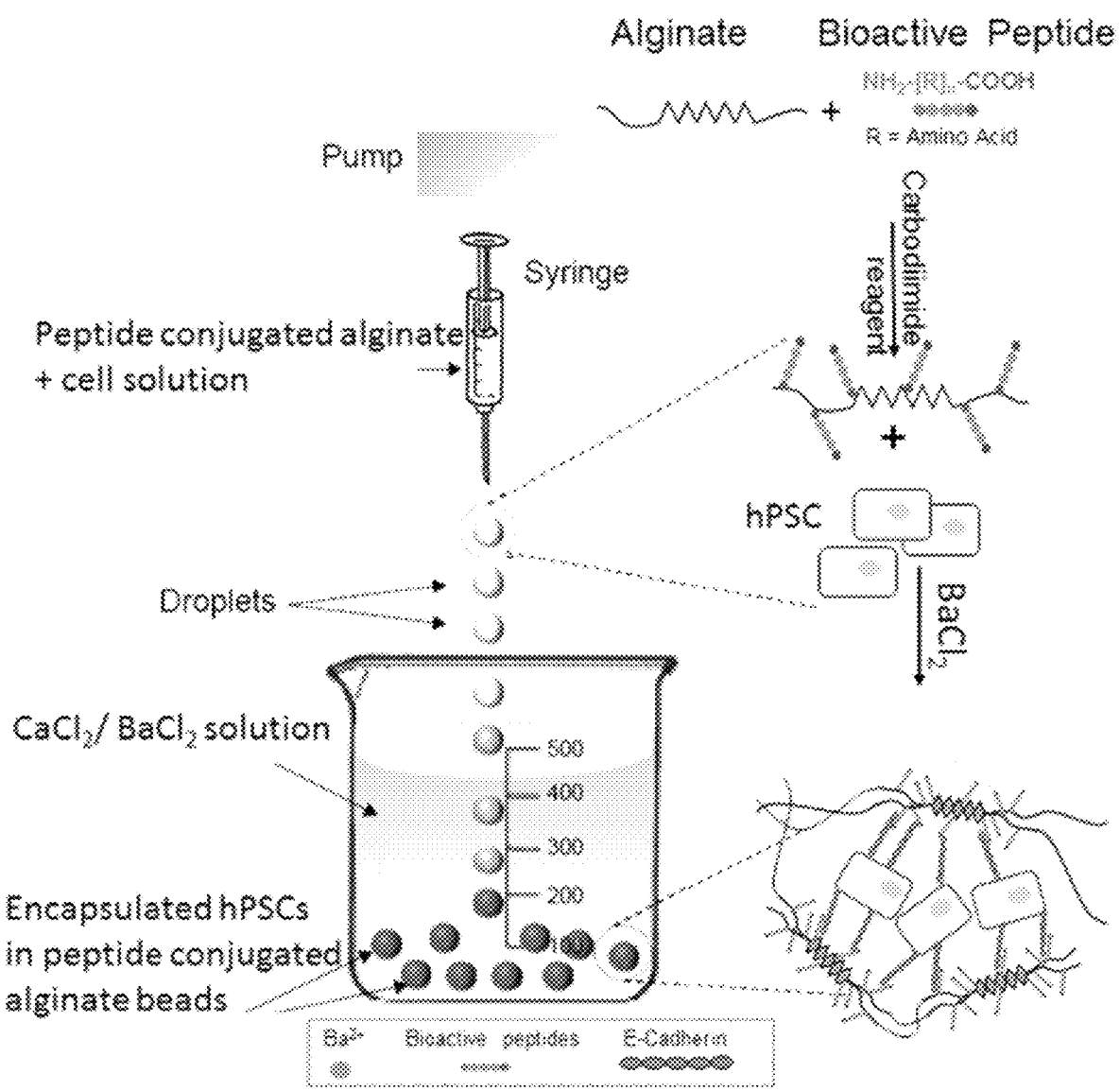
FIG. 3 is a schematic diagram of an exemplary encapsulation process with modified alginate.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, "pluripotent stem cells" are cells that have the capacity to self-renew by dividing and to develop into the three primary germ cell layers of the early embryo and therefore into all cells of the adult body, but not extra-embryonic tissues such as the placenta. "Human pluripotent stem cells (hPSCs)" are pluripotent stem cells able to develop into the three primary germ cell layers of the early human embryo and therefore into all cells of the adult human body, and include human embryonic stem cells (hESCs) and human induced pluripotent stem cells (hiPSCs). hESCs are derived from the inner cell mass of cultured preimplantation human blastocysts. iPSC are derived from, e.g., skin or blood cells that have been reprogrammed back into a pluripotent state that enables the development of an unlimited source of any type of human cell needed for therapeutic purposes. Human somatic cells can be reprogrammed into hiPSCs by methods including: ectopic expression of transcription factors, ectopic expression of transcription factors together with small molecules; and ectopic expression of microRNAs (See, e.g., Zhu, Z, et al. Human pluripotent stem cells: an emerging model in developmental biology, *Development*. 2013 Feb. 15; 140(4): 705-717).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A chemical structure incorporated into a larger chemical structure, or a portion of a chemical structure is a "moiety". A polymer is said to comprise a specific type of linkage, such as an ester, amide, or urethane linkage, if that linkage is present in the polymer. A protein, peptide, or oligopeptide is a chain comprising two or more amino acid residues connected by a peptide (amide) bond, where the sequence of the amino acid is designated by conventional single-letter codes, and can also be referred to by conventional three-letter codes (e.g. G and gly refer to glycine; H and his refer to histidine; A and ala refer to alanine; V and val refer to valine; etc.).

A "hydrogel" is a two-phase composition comprising a hydrophilic, polymeric composition containing synthetic or naturally derived organic moieties capable of absorbing, retaining, containing, or otherwise comprising water or biological fluids. A large variety of well-known polymer compositions are cytocompatible as well as biocompatible, and can form hydrogels, which can be modified/functionalized with a peptide according to aspects of the invention as described herein. Non-limiting examples of such hydrogels include: natural or synthetic polysaccharides, e.g. as described herein, polyacrylates, and polyacrylamides, among a large variety of other useful hydrophilic polymer compositions. Non-limiting examples of acrylates include poly(acrylic acid), poly(methacrylic acid).

Further, as used herein, the terms "over", "formed over", "deposited over", or "provided over" mean formed, deposited, or provided on but not necessarily in contact with a surface or layer. For example, a coating layer "formed over" a substrate or layer does not preclude the presence of one or more other coating layers or films of the same or different composition located between the formed coating layer and the substrate. Likewise, the terms "under" or "between" in the context of specified coating layers does not preclude the presence of one or more other coating layers or films of the same or different composition located between the recited layers.

Polypeptides can be linked to the polysaccharide, such as a polysaccharide comprising pendant carboxyl groups, by any effective means, and using zero-length (linked directly), or non-zero-length crosslinkers. "Carbodiimide chemistry" is a common and versatile method of zero-length crosslinking of primary amines to carboxyl groups. Carbodiimide chemistry leaves an amide bond (—C(O)NH—) between the two linked moieties. Common carbodiimides include EDC (1-ethyl-3-(-3-dimethylaminopropyl) carbodiimide hydrochloride) and DCC (N',N'-dicyclohexyl carbodiimide).

Polysaccharides comprise a plurality of, e.g. a chain of, e.g., monosaccharide units (e.g. 3-7-member rings), or disaccharide units (comprising two different monosaccharides), bound by glycosidic bonds or linkages, and can be linear or branched. An anionic polysaccharide is a polysaccharide having a negative charge, for example and without limitation an overall charge of $-1$, $-2$, $-3$, $-4$, $-10$, etc., and a polyanionic polysaccharide has a plurality of negative charges, for example and without limitation an overall charge of $-2$ or less, e.g., $-2$, $-3$, $-4$, $-10$, etc. A carboxylated polysaccharide is a polysaccharide that either naturally, or by synthetic methods, comprises a plurality of pendant carboxyl (—COOH) groups. Non-limiting examples of carboxylated polysaccharides include, without limitation, alginate (alginic acid), guar gum, carboxymethylcellulose (CMC), hyaluronic acid, pullulan, carrageenan, pectin, acid modified chitosan, xanthan gum, agarose, and mixtures thereof. In carboxylated polysaccharides, all or a portion of the monosaccharide units of the polysaccharide may be carboxylated. In the context of the compositions described herein where the polysaccharide is linked to a peptide, the polysaccharide comprises, or comprised prior to linking to the polypeptide, pendant carboxyl groups. The presence of pendant carboxyl groups in such a composition would depend on whether or not all pendant carboxyl groups of the polysaccharide were modified with a peptide.

A polyamine is a polymer comprising a plurality of amine groups, including primary amines, secondary, and tertiary amines. Amines are capable of forming cationic ammonium ions. A non-limiting example of a polyamine is a poly (allylamine), such as poly(allylamine) hydrochloride.

A polyalkylenimine is a branched or linear polymer compound comprising primary, secondary and/or tertiary amines linked by alkyl groups, such as linear or branched ethyl or propyl groups, including the divalent, saturated ethylene and n-propylene groups. As an example, polyethylenimine (e.g. polyaziridine) comprises ethylene moieties (portions of larger molecules) and amine moieties, and can be, for example, linear, branched, or dendrimeric (e.g. star- or sphere-shaped).

In the composition described herein in which a peptide, e.g., of 100 or less amino acids, 50 or less amino acids, or 25, 20, or 15 or less amino acids, is linked to the polysaccharide, e.g., the carboxylated polysaccharide, all pendant carboxyl groups, or a portion of carboxyl groups are linked to the peptide. Where less than all pendant carboxyl groups are linked to the peptide, free carboxyl groups remain. Where not all pendant carboxyl groups are linked to the peptide, or not all monosaccharide moieties of the polysaccharide comprise pendant carboxyl groups, for example, 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of the monosaccharide moieties (rings) of the polysaccharide have the peptide linked thereto.

The methods, material, and conjugation design platform described herein allows for single cell survival and hence clonal expansion of hPSCs. The described technology is a low cost synthetic peptide conjugated hydrogel system for hPSC biomanufacturing. hPSCs form colonies through the cell adhesion molecule E-cadherin. Loss of E-cadherin junction triggers the apoptotic pathway and cell death. E-cadherin binding is mimicked using short amino-acid peptides. As an example, the peptide HAV10 (amino acid sequence: LFSHAVSSNG (SEQ ID NO: 2)) is a binding sequence of the extracellular EC1 domain of the full E-cadherin protein. HAV10 is attached to alginate, using aqueous carbodiimide chemistry, which creates an amide bond between the carboxylate groups of alginate and the amine group on the N-terminus of the peptide. This peptide-modified alginate can be used to promote single-cell hPSC culture in lab-scale 2D (planar, adherent) systems or large scale 3D (spheroidal, suspension) systems.

According to one aspect, the technology includes: conjugation of HAV10 or another E-cadherin extracellular domain peptide fragment to alginate; HAV10 or another E-cadherin extracellular domain peptide fragment used for hPSC culture (single cell or colonies) when bound to alginate; HAV10 or another E-cadherin extracellular domain peptide fragment bound to alginate for improving the survival of single hPSCs; and Propagation of hPSCs in peptide conjugated alginate capsule. One advantage of mimicking cell-cell contact in this manner is the enhancement of cell viability and pluripotency, and hence the method and compositions can be used for scalable culture and propagation of hPSCs.

In addition, contemporary approaches have other limitations which can be overcome by the suspension culture approach described herein. Planar cultures are limited in their throughput. In contrast, suspension cultures have higher throughput, but the dynamic culture environment often negatively affects cell growth and differentiation. The 3D approach described herein encapsulates the hPSCs within the modified substrate capsules, enabling suspension culture with high throughput. The capsules protect the encapsulated cells from the external hydrodynamic shear stress in the bioreactor. It also prevents agglomeration of cell aggregates. This allows for higher density of culture, higher agitation speed while maintaining a controlled cell environment. Overall, the advantages of the innovation described herein include: use of xeno-free, chemically-defined synthetic peptides; use of FDA-approved alginate substrate; overall low cost of modified substrate; high viability of single cell hPSC culture, which increases the efficiency of the starting hPSC population for large scale expansion; capsules protect hPSCs from hydrodynamic forces imparted during large scale expansion and culture; capsules prevent hPSC over-aggregation, which ultimately provide a pure population of undifferentiated hPSC for differentiation to therapeutic cell types; and the conjugation approach is versatile and can be extended to any polysaccharide-based natural or synthetic polymer-derived hydrogel systems amenable for hPSC culture.

E-cadherin (epithelial cadherin, also referred to as Cadherin 1, encoded by the CDH1 gene) is a calcium-dependent cell-cell adhesion protein comprised of five extracellular cadherin repeats, a transmembrane region and a highly conserved cytoplasmic tail. E-cadherin dimerizes through completion of a trans interaction between adjacent EC1 domains which contains either a 'bulge' region consisting of a conserved HAV peptide sequence or 'groove' regions through the ADT sequence (Sinaga E J, et al. Increasing paracellular porosity by E-cadherin peptides: discovery of bulge and groove regions in the EC1-domain of E-cadherin. *Pharm Res* 2002; 19:1170-9; Chappuis-Flament S, Multiple cadherin extracellular repeats mediate homophilic binding and adhesion. *J Cell Biol* 2001; 154:231-43; and Renaud-Young M, et al. In the first extracellular domain of E-cadherin, heterophilic interactions, but not the conserved His-Ala-Val motif, are required for adhesion. *J Biol Chem* 2002; 277:39609-16) (FIG. 1A). These and other sequences, based on overlapping dimers of various EC1-5 domains, have resulted in a variety of sequences that result in binding of E-cadherin of various cell types (Sinaga E J, et al. Increasing paracellular porosity by E-cadherin peptides: discovery of bulge and groove regions in the EC1-domain of E-cadherin. *Pharmaceutical research.* 2002; 19:1170-9; Kobayashi N, et al. Inhibition of e-cadherin-mediated homotypic adhesion of Caco-2 cells: a novel evaluation assay for peptide activities in modulating cell-cell adhesion. *J Pharmacol Exp Ther* 2006; 317:309-16; and Chen T, et al. E-cadherin-mediated cell-cell contact is critical for induced pluripotent stem cell generation. *Stem cells* 2010; 28:1315-25). The EC1 domain has been previously shown to be the primary E-cadherin subunit involved in cell-cell contact (Boggon T J, et al., C-cadherin ectodomain structure and implications for cell adhesion mechanisms *Science* 2002; 296:1308-13 and Parisini E, et al., The crystal structure of human E-cadherin domains 1 and 2, and comparison with other cadherins in the context of adhesion mechanism. *J Mol Biol* 2007; 373:401-11).

The compositions described herein comprise a polypeptide comprising a cell-binding sequence of an epithelial cadherin extracellular domain, such as a bulge or groove sequence of the EC1 domain of epithelial cadherin. The polypeptide ranges from five to 100 amino acids in length, from five to 75, 50, 25, 20, 15, or 10 amino acids in length, for example and without limitation 5, 6, 7, 8, 9, 10, 11, 12, 13, 14, 15, 16, 17, 18, 19, 20, 21, 22, 23, 24, or 25 amino acids in length. The polypeptide comprises: the sequence LFSHAVSSNG (SEQ ID NO: 2), SHAVSS (SEQ ID NO: 3), QGADTPPVGV (SEQ ID NO: 4), and/or ADTPPV (SEQ ID NO: 5), the sequence HAV or ADT, a sequence having at least five consecutive amino acids of SHAVSS (SEQ ID NO: 3) and/or ADTPPV (SEQ ID NO: 5), and/or a sequence having at least 80% sequence identity with SHAVSS (SEQ ID NO: 3) and ADTPPV (SEQ ID NO: 5). For example, the polypeptide includes the sequence LFSHAVSSNG (SEQ ID NO: 2), SHAVSS (SEQ ID NO: 3), QGADTPPVGV (SEQ ID NO: 4), and/or ADTPPV (SEQ ID NO: 5), a sequence comprising the amino acid sequence HAV or ADT, a sequence having at least five consecutive amino acids of SHAVSS (SEQ ID NO: 3) and/or ADTPPV (SEQ ID NO: 5), or a sequence having at least 80% sequence identity with the sequences SHAVSS (SEQ ID NO: 3) and ADTPPV (SEQ ID NO: 5), the sequence further having, consisting essentially of, or consisting of, an amino acid sequence that has at least 80%, 85%, 90%, 95%, or 100% sequence identity with from six to 25, e.g., 6, 7, 8, 9, 10, 11, 12, 13, 14, 15, 16, 17, 18, 19, 20, 21, 22, 23, 24, or 25, consecutive amino acids of a human epithelial cadherin (For example and without limitation, see FIG. 6) and comprises the HAV and/or ADT sequences. Sequences other than LFSHAVSSNG (SEQ ID NO: 2), SHAVSS (SEQ ID NO: 3), QGADTPPVGV (SEQ ID NO: 4), and/or ADTPPV (SEQ ID NO: 5), a sequence comprising the amino acid sequence HAV or ADT, a sequence having at least five consecutive amino acids of SHAVSS (SEQ ID NO: 3), and/or ADTPPV (SEQ ID NO: 5), or a sequence having at least 80% sequence identity with the sequences SHAVSS (SEQ ID NO: 3) and ADTPPV (SEQ ID NO: 5) may be included in the polypeptide so long as are capable of supporting hPSC propagation, that is, compared to the polypeptides LFSHAVSSNG (SEQ ID NO: 2), SHAVSS (SEQ ID NO: 3), QGADTPPVGV (SEQ ID NO: 4), and/or ADTPPV (SEQ ID NO: 5), they retain and/or do not interfere to any substantial extent, with the ability of the polypeptide to function as described herein as part of the described composition useful for hPSC propagation.

Those of ordinary skill in the art can prepare polypeptides by a number of useful methods, such as by chemical synthesis, such as by broadly-known liquid-phase, or solid-phase chemistries. Custom synthetic peptides ranging beyond 100 amino acids in length can be ordered and purchased from any of a large number of commercial sources. Recombinant methods, as are broadly-known, also can be used to produce polypeptides, though typically larger polypeptides amendable to recombinant production methods are made in this manner. Further description of chemical and recombinant synthesis methods are unnecessary as these methods are broadly-known to those of ordinary skill in the art, and in view of the large number of commercial resources available to manufacture custom polypeptides. The described variations in the sequences as described above can be readily tested by those of ordinary skill by, for example and without limitation, using the assays described in the examples below and observing the ability to propagate hPSCs that exhibit the ability to differentiate.

Linkage of the polypeptide to the hydrogel, e.g. polysaccharide may be accomplished by any effective mechanism, such as by carbodiimide chemistry as described herein, or through use of another acceptable linker and/or linking chemistry. Linking chemistries and linker compositions are broadly-known to those of ordinary skill.

Described in the Examples below are findings on (i) how substrate properties can influence viability of encapsulated hPSCs in 3D aggregate culture, and (ii) the effect of conjugation chemistry on hPSC viability in adherent 2D cultures. In aspects of the composition described herein, incorporation of the divalent ion cross-linking of alginate (Alg) contributes to both physical (stiffness, porosity, pore size, distribution and compliance) changes as well as chemical (surface and bulk) compositional changes that contribute to hPSC viability and response. These effects are seen as shown in both bulk (3D) as well as surface (2D) configurations. With respect to another aspect, the specific sequence polyethylenimine (poly (allylamine hydrochloride)/Alg) (PEI(PAH/Alg)), with the coupling concentration and composition of the conjugated peptide on the resulting substrate surface presented to the hPSC dictate the response as shown. Other sequences of layer-by-layer films with the coupling of the peptide and the effects of the resulting substrate surface presented to the hPSC have also been explored. Specifically, the number of layers used to form the film (n) has been varied, in addition to exploring other polycationic solutions for film formation, such as but not limited to poly-1-lysine (PLL) containing positively charged functional groups.

According to one aspect of the invention, provided herein is a composition for use in propagating pluripotent stem cells from single cells, comprising: a hydrogel, e.g. a biocompatible polysaccharide hydrogel; and a polypeptide comprising a cell-binding sequence of an epithelial cadherin extracellular domain linked (covalently bound) to the hydrogel, wherein the polypeptide optionally consists of 100 or less amino acids. In one aspect, the polysaccharide is carboxylated (comprising one or more, e.g., two or more, pendant carboxyl groups, examples of which include, without limitation, alginate (alginic acid), guar gum, carboxymethylcellulose (CMC), hyaluronic acid, pullulan, carrageenan, pectin, acid modified chitosan, xanthan gum, agarose, and mixtures therein). In one aspect, the polypeptide comprises the amino acid sequence LFSHAVSSNG (SEQ ID NO: 2), as an example, the polypeptide consist of the amino acid sequence the sequence LFSHAVSSNG (HAV10, SEQ ID NO: 2), SHAVSS (HAV6, SEQ ID NO: 3), QGADTPPVGV (ADT10, SEQ ID NO: 4), and/or ADTPPV (ADT6, SEQ ID NO: 5). In other aspects, the polypeptide comprises: the sequence HAV or ADT, a sequence having at least five consecutive amino acids of SHAVSS (SEQ ID NO: 3) and/or ADTPPV (SEQ ID NO: 5), and/or a sequence having at least 80% sequence identity with SHAVSS (SEQ ID NO: 3) and ADTPPV (SEQ ID NO: 5). In another aspect, the polypeptide is linked directly to the polysaccharide by an amide bond. In yet another aspect, the composition comprises free carboxyl groups, that is carboxyl groups that were not reacted with the polypeptide—for example and without limitation, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties (e.g., rings) of the polysaccharide have the peptide linked thereto. In a further aspect, the polypeptide-conjugated polysaccharide comprises viable pluripotent cells and is optionally cross-linked with calcium or barium.

Also provided is a method of propagating pluripotent cells, such as hESCs, comprising depositing pluripotent stem cells (e.g., single (dissociated) cells) onto, or mixing the cells with, a composition comprising a polypeptide-conjugated hydrogel, e.g. polysaccharide composition as described herein, such as, for example, the alginate-HAV10 composition described herein, and culturing the cells with appropriate stem cell medium, thereby expanding a population of the pluripotent cells. The cells optionally are first cultured in suitable medium in the presence of a rho-associated, coiled-coil containing protein kinase (ROCK) inhibitor, such as Y-27632, shown below.

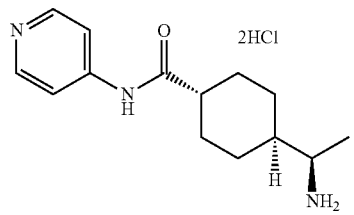 [SMILES: C[C@@H](N)[C@H]1CC[C@H](C(=O)Nc2ccncc2)CC1]

Prior to culturing the cells, the peptide-conjugated polysaccharide and cells are mixed and dropped into a solution of barium or calcium ions/salts (e.g., chlorides), for example a 15 mM or less solution of BaCl2 or 100 mM $CaCl_2$ to encapsulate the cell-containing composition, and then culturing the encapsulated cells in suitable cell culture medium, optionally exposing the cells to a ROCK inhibitor in the first 1, 2, 3, or 4, days of culture.

Other ROCK inhibitors include fasudil (5-(1,4-Diazepane-1-sulfonyl)isoquinoline), e.g. fasudil hydrochloride, for treatment or cerebral vasospasm, and ripasudil, e.g. rupasudil hydrochloride, for treatment of glaucoma. Several different classes of Rock Inhibitor have been synthesized for different therapeutic applications (reviewed in Feng, Y., et al. Rho Kinase (ROCK) Inhibitors and Their Therapeutic Potential, *J. Med. Chem.*, 2016, 59, 2269-2300). The structures of the ROCK inhibitors fasudil, ripasudil, thiazovivin (N-benzyl-2-(pyrimidin-4-ylamino)thiazole-4-carboxamide), and GSK429286A (4-[4-(Trifluoromethyl)phenyl]-N-(6-Fluoro-1H-indazol-5-yl)-2-methyl-6-oxo-1,4,5,6-tetrahydro-3-pyridinecarboxamide) are shown below.

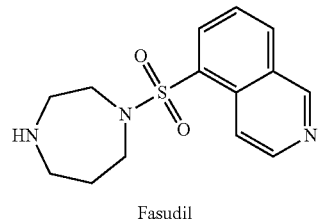

Fasudil

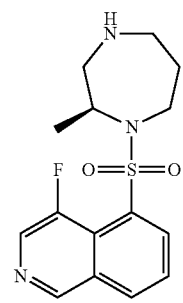

Ripasudil

-continued

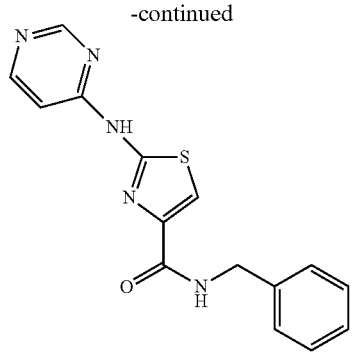

Thiazovivin

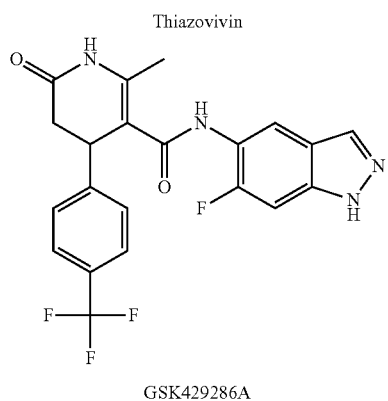

GSK429286A

Lastly a method of preparing a cell growth composition is provided, comprising conjugating a polypeptide, according to any aspect described herein, with a hydrogel, e.g. a polysaccharide, such as a carboxylated polysaccharide, to produce a polypeptide-conjugated polysaccharide; mixing cells, such as pluripotent cells, such as hESCs, with the polypeptide-conjugated polysaccharide; optionally exposing the cells mixed with the polypeptide-conjugated polysaccharide to a solution of a divalent cation, such as barium or calcium ions, e.g. a salt, such as a calcium chloride or barium chloride solution, optionally less than or equal to 15 mM, to produce encapsulated cells; and culturing the cells in cell culture medium, such as stem cell medium, optionally exposing the cells in culture to a ROCK inhibitor, such as Y-27632, within the first 1, 2, 3, or 4, days of culture, thereby expanding the cells, wherein when the cells are pluripotent, the cells retain their pluripotency. In one aspect, the polypeptide as described above, e.g., HAV10, HAV6, ADT10, or ADT6, or combinations thereof, is conjugated with a carboxylated polysaccharide, e.g., alginate, by carbodiimide chemistry such that the polypeptide-conjugated carboxylated polysaccharide comprises a plurality of pendant carboxyl groups unreacted with the polypeptide, and/or the polypeptide-conjugated carboxylated polysaccharide is reacted with a low amount of carbodiimide, for example less than <100 mM, <50 mM, <25 mM, <10 mM, or <5 mM of the carbodiimide, e.g. EDC or DCC, for example from 0.11-10 mM, e.g., 4 mM EDC.

Figure 7A:
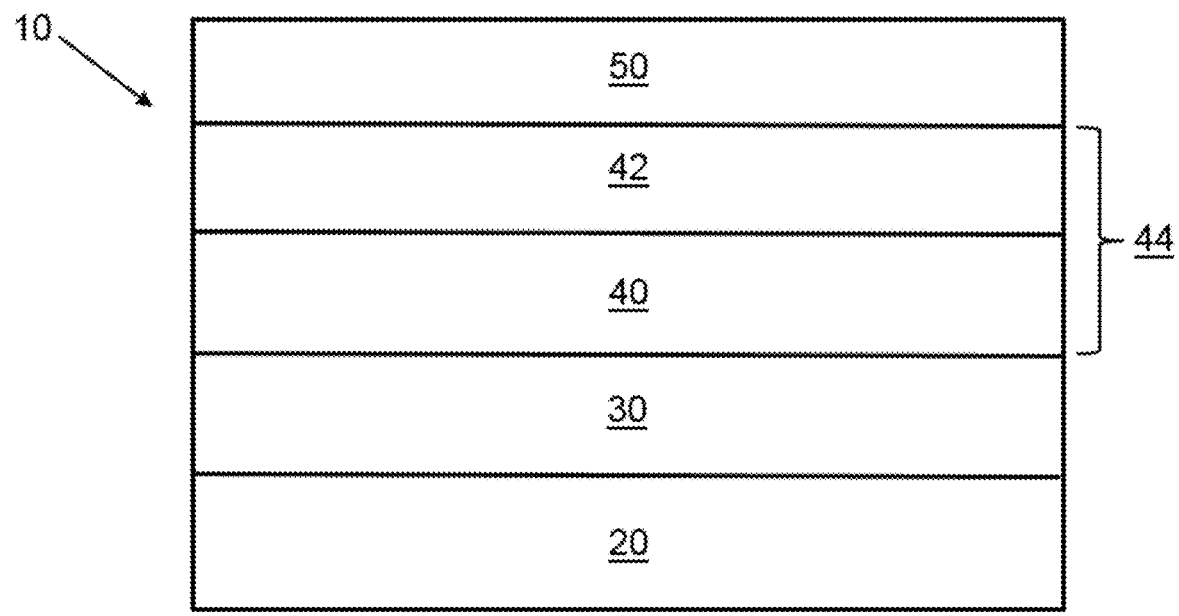
FIGS. 7A and 7B provide schematic diagrams of a device as described herein.
Figure 7B:
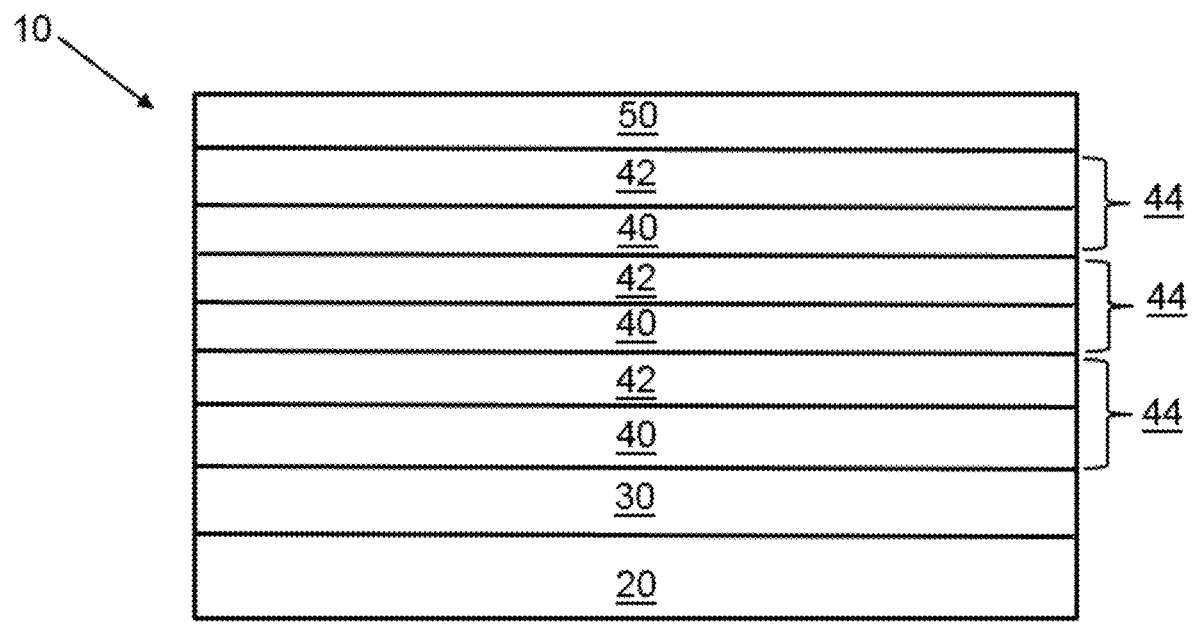

In one aspect, a multi-layered device is prepared. As shown schematically in FIG. 7A (not to scale), device 10, comprises a substrate 20, a cationic polymeric layer 30 (optional), such as a polyethylenimine (PEI) layer, over the substrate 20. A first anionic polysaccharide layer 40 over the cationic polymeric layer 30, a second cationic polymeric layer 42 over the first anionic polysaccharide layer 40, and a second anionic polysaccharide layer 50 over the second cationic polymeric layer 42. Intermediate layers 44, including the first anionic polysaccharide layer 40 and the second cationic polymeric layer 42 may be repeated, for example 1, 2, 3, 4, 5, 6, 7, 8, 9, or 10 times, or more (see FIG. 7B, showing three iterations of intermediate layers 44). Substrate 20 can be any effective substrate of any useful size or shape, such as a planar surface as is found in tissue culture plates and flasks, tubes, porous or non-porous beads, filaments, etc. and can be manufactured from any useful biocompatible material, including polymer(s), ceramic(s), metal(s), glass, carbon structures, or combinations thereof.

Example 1—Data Supporting Effect of Cross-Linking Concentration on Hpscs Encapsulated in 3D Beads We have demonstrated that hPSCs encapsulated in alginate beads in three dimensional (3D) configuration are highly sensitive to the crosslinking concentration of the bead. As illustrated in FIG. 4, a specific range of Barium Chloride ($BaCl_2$) concentration (<15 mM) is supportive and strongly inductive of hPSC growth. While higher values of $BaCl_2$ concentration (15 mM) and less conducive for hPSC growth.

Encapsulation Methods:

hESCs were encapsulated using 10, 15, 20, 50 or 100 mM $BaCl_2$ at a seeding density of $1\times10^6$ cells/ml of alginate solution. Alginate capsules were incubated for 6-8 min in the $BaCl_2$ solution. Capsules were washed three times with DMEM/F12 and suspended in mTeSR1 (STEMCELL Technologies, Vancouver, BC) with 10 mM of the ROCK inhibitor (rho-associated, coiled-coil containing protein kinase inhibitor) Y-27632 (e.g., 4-[(1R)-1-aminoethyl]-N-4-pyridinyl-trans-cyclohexanecarboxamide, dihydrochloride, STEMCELL Technologies, Vancouver, BC) for 4 days, followed by 2 days in mTeSR1 alone to allow for colony formation. On day 6, viability of encapsulated hPSCs was analyzed by LIVE/DEAD staining, and imaged with fluorescent microscopy. The stock LIVE images from LIVE/DEAD analysis were processed using Metamorph Integrated Morphometry Analysis. hPSC colony data was generated for each colony within each image, measuring the area of the colony. This image processing was done on images taken on 5 capsules, each day for each condition.

Example 2—Data Supporting Effect of EDC/NHS Concentration

Our initial studies show mild toxicity of 1-ethyl-3-(-3-dimethylaminopropyl) carbodiimide hydrochloride (EDC)/N-hydroxysuccinimide (NHS) towards hPSC attachment and viability. As illustrated in FIG. 5, a lower concentration of EDC/NHS resulted in cell attachment comparable to the gold standard of Matrigel; increasing the concentration to 100 fold resulted in a drop in initial hPSC attachment and cell viability.

Preparation of PAH/Alg Coating.

Layer-by-layer (LBL) coating onto glass coverslips was initiated by incubation in 1.1 mg/ml Polyethylenimine (PEI) for 5 min. The polyelectrolyte solutions used for LBL deposition were 1.1 mg/ml low viscosity alginate (Alg) and poly (allylamine hydrochloride) (PAH), made using 0.1 M 2-(N-morpholino) ethanesulfonic acid (MES) buffer with 0.3M NaCl at pH 6.5. Polyelectrolyte multilayers were deposited by alternatively immersing slides into Alg, followed by PAH, for 1 min each, and were subsequently washed with 0.9% NaCl for 1 min between each deposition step. This process was repeated for 5 Alg/PAH layers, and the film was terminated with a final Alg layer (PEI(Alg/PAH)$_5$Alg). Coverslips were dried at room temperature until used.

Peptide Conjugation of LBL Films and Cell Attachment.

Prepared PEI(Alg/PAH)$_5$Alg films were functionalized with the e-cadherin mimicking peptide HAV10 using water soluble carbodiimide chemistry. Films were incubated with 400 mM/200 mM EDC/NHS for 15 min to initiate chemical coupling for peptide immobilization. The peptide (10 μg/ml) was then added in the presence of EDC/NHS overnight at 4° C. Slides were washed 3 times with PBS, and exposed to UV light for 30 min for sterilization, before adding cells. For cell experiments, coverslips were placed in the wells of a 48-well plate.

Human embryonic stem cells (hESCs) were treated with the ROCK inhibitor Y-27632 for 2 hours prior to harvesting. hESCs were harvested using enzyme-free dissociation buffer and were treated with the Vibrant DiD cell labeling solution, to allow for visualization of cell attachment (700 nm). DiD-labeled hESCs were seeded onto the peptide modified LBL films at a density of 5×10$^4$ cells/well of a 48 well plate, and cultured at 37° C., 5% CO$_2$, and 95% relative humidity for 6 hours to allow for cell attachment. After 6 hours the cells were imaged using the LI-COR Odyssey scanner to obtain the mean fluorescent intensity (MFI) of the total possible number of cells/well. Unattached or dead cells were washed away using DMEM/F12, and the cells were imaged a second time to obtain the MFI of only the attached cells. Cell attachment for each condition was determined by normalizing the MFI of attached cells to the MFI of the total possible number of cells, for each well imaged.

Example 3

The objective of this study was to functionalize alginate hydrogels with synthetic peptides mimicking E-cadherin (Table 1) and evaluate peptide performance in promoting cell attachment, viability, maintaining pluripotency, and differentiation potential. Alginate conjugated with HAV- and ADT-based peptides (peptides comprising the HAV or ADT amino acid sequences) supported initial cell attachment and hPSC propagation. Cells propagated on the peptide modified substrates maintained good pluripotency and differentiation potential, as shown by gene and protein analysis.

TABLE 1

E-cadherin mimicking peptides and sequences.

| Name | Sequence | Description |
|---|---|---|
| HAV10 | LFSHAVSSNG (SEQ ID NO: 2) | Groove EC1 10 peptide |
| HAV6 | SHAVSS (SEQ ID NO: 3) | Groove EC1 6 peptide |
| ADT10 | QGADTPPVGV (SEQ ID NO: 4) | Bulge EC1 10 peptide |
| ADT6 | ADTPPV (SEQ ID NO: 5) | Bulge EC1 6 peptide |

Materials and Methods hPSC Culture.

Undifferentiated (UD) H1 hESCs (WiCell) were maintained on hESC-qualified Matrigel (BD Biosciences) coated tissue culture plastic for 5-7 days in mTeSR1 (StemCell Technologies) at 37° C. and 5% CO$_2$ before passaging. Experiments were performed with p55-p85 hESCs.

Thin Alginate Hydrogel Formation and Peptide Conjugation.

The alginate hydrogels were formed prior to peptide attachment. The culture well was coated with a thin layer of 1.1% (w/v) low viscosity alginate (Sigma-Aldrich) with 0.2% (v/v) gelatin (Sigma-Aldrich), which was allowed to dry overnight. 20 mM BaCl$_2$ was used to rehydrate and simultaneously cross link the alginate in a thin hydrogel covering the bottom of the culture well. Peptide conjugation was done using water soluble carbodiimide chemistry [26]. Alginate hydrogels were activated by incubating with 20 mM/10 mM EDC/NHS in buffer containing 0.3 M 2-(N-morpholino) ethanesulfonic acid (MES) and 0.1 M NaCl, for 15 min. The peptides were then added and incubated overnight at 4° C. to allow for peptide conjugation to the carbonyl groups of the alginate hydrogel. After conjugation, peptide modified hydrogels were washed with 0.9% saline prior to seeding cells.

Confirmation of peptide conjugation to the alginate hydrogels was done using the BCA assay, according to manufacturer's instructions. Briefly, peptide conjugated alginate hydrogels were incubated with BCA reagent at 60° C. for 30 min. The resulting supernatant absorbance analyzed using a Synergy 2 multi-mode Microplate Reader (BioTek, Winooski, Vt., USA).

Cell Attachment. For cell attachment studies to the peptide modified hydrogels, hESC were first labeled with DiD according to manufactures instruction, a fluorescent lipophilic dye, which is incorporated in the cell membrane. hESC were treated with 10 μm Y-27632 (R&D Systems, Minneapolis, Min.) for 2 hours prior to harvesting by Accutase (Invitrogen) treatment for 5-7 min. For cell attachment, studies were performed in a 48 well plate, seeded with 50,000 cells/well. Cell attachment was analyzed 24 hours after seeding. First, total cell number per well was quantified using the LI-COR Odyssey scanner and Image Studio software to obtain the total possible MFI. Dead and unattached cells were washed away and the number of attached cells per well was again quantified using the LI-COR Odyssey scanner Image Studio software. Cell attachment data was presented as percent attachment by normalizing the attached cell MFI to the total cell MFI for each peptide and peptide concentration.

LIVE/DEAD Assay.

LIVE/DEAD (Life Technologies) viability assay was performed according to manufacturer's instructions.

Cell Expansion.

To determine cell expansion, cellular metabolism was assayed on cells attached to alginate conjugated with 50 μg/ml of each peptide using the CellTiter 96® AQ$_{ueous}$ One Solution Cell Proliferation Assay (MTS) after 1 and 6 days of culture, according to manufacturer's instructions. Briefly, cells were incubated with the MTS solution at a 1:5 v/v dilution for 3 hours at 37° C. Absorbance intensity of the supernatant at 490 nm was measured using a Synergy 2 multi-mode Microplate Reader. Fold expansion was determined by normalizing the day 6 absorbance by the day 1 absorbance, for cells grown on each peptide-conjugated alginate substrate.

Directed Differentiation.

hESC seeded on the peptide modified alginate hydrogels were propagated for 4 days in mTeSR1 with 10 μm Y-27632 prior to DE induction. DE was induced using 100 ng/ml ActivinA (R&D Systems) with 25 ng/ml Wnt3A (R&D Systems) for 4 days. Quantitative Reverse Transcriptase Polymerase Chain Reaction. mRNA was isolated using the NucleoSpin RNA II kit (Macherey-Nagel, Bethlehem, Pa.). cDNA was obtained using ImpromII Reverse Transcription (Promega, Madison, Wis.). Each PCR reaction contained 5 µl SYBR Green Master Mix (Agilent, Santa Clara, Calif.), 2 µl nuclease free $H_2O$, 2 µl primer, and 10 cDNA. Samples were normalized to the house keeping gene GAPDH and analyzed relative to UD hESCs using the $\Delta\Delta Ct$ method. Gene expression was measured with quantitative polymerase chain reaction (qRT-PCR) using an MX3005P system (Agilent).

Immunostaining.

Cells were fixed with 4% formaldehyde for 20 min, and were permeabilized with 0.1% Triton-X (Sigma) in 0.9% saline for 5 min. A blocking step with 10% donkey serum in 0.9% saline was done for 1 hour. For primary antibody staining, we used goat anti-Nanog (1:200 dilution, Cell Signaling, Danvers, Mass.). The incubation time for primary antibodies was done overnight at 4° C. Cells were incubated with the secondary antibody for 45 min at room temperature. For secondary antibody staining, we used anti-goat Alexafluor 488 (1:500 dilution). Cells were washed three times with 0.9% saline (5-10 min) before mounting on slides with hardening mounting medium containing DAPI (Vectashield, Vector laboratory). Imaging was done using a Nikon A1 confocal microscope.

Statistical Analysis.

Statistical significance comparing multiple groups was determined using one-way ANOVA, with Tukeys or Games-Howell post hoc testing for homogeneous or inhomogeneous variance, respectively. Probability values at P<0.05(*) and P<0.01 (**) indicated statistical significance.

Results

Substrate Design and Characterization.

Figure 8:
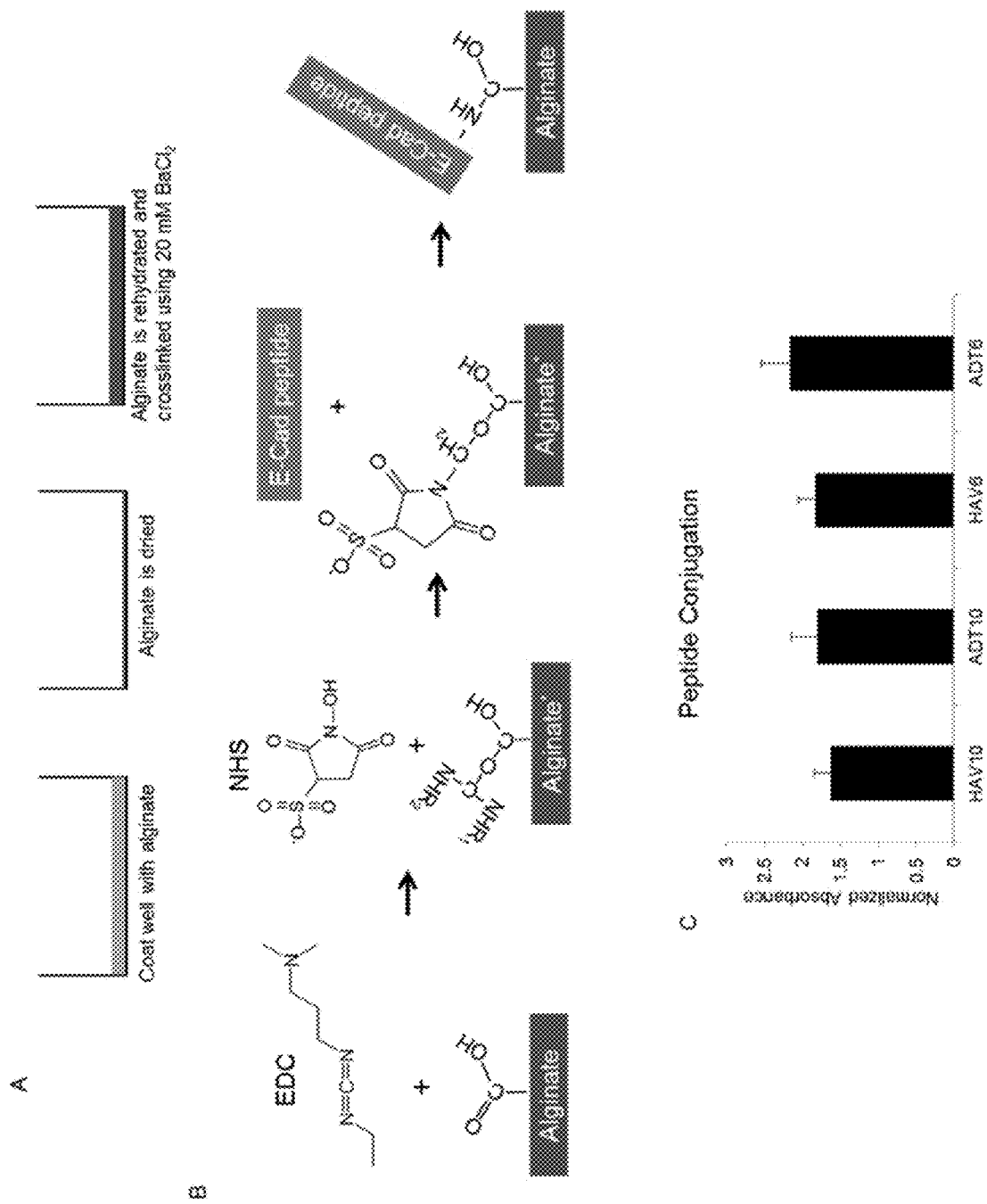
FIG. 8. Schematic of peptide conjugated alginate hydrogel and characterization. A) Schematic of thin alginate hydrogel formation in a well plate. B) Carbodiimide chemistry was used to activate the carboxylic acid groups on alginate, making them reactive and able to form a peptide bond with the N-terminus of the desired peptide. C) BCA protein assay analysis confirming the attachment of the peptides to the thin alginate hydrogel.

A thin alginate hydrogel was created by first coating tissue culture wells with a 1.1% alginate solution, allowing this coating to dry, and finally rehydrating the dried alginate using 20 mM $BaCl_2$ (FIG. 8A).

The $BaCl_2$ crosslinks the alginate as it is being rehydrated, which resulted in a thin alginate hydrogel covering the entire culture surface, thus preventing cells from getting underneath the gel between the tissue culture plastic and hydrogel. Peptide conjugation was achieved by first activating the alginate hydrogel using 20/10 mM EDC/NHS (FIG. 8B). The EDC activates the carbonyl groups of the alginate back bone, forming an unstable o-Acylisourea intermediate. This intermediate is stabilized by the addition of the NHS, forming a reactive sulfo-NHS ester group on the carboxylic acid groups of the alginate substrate, allowing for peptide bond formation with the N-terminus of the e-cadherin peptides.

Peptide conjugation to the alginate hydrogel was confirmed using the BCA assay (FIG. 6C). The peptide bonds between the amino acids in the peptides cause the reduction of $Cu^{+2}$ in the BCA reagent to $Cu^{+1}$. This chelates the BCA reagent, and thus, in the presence of the peptide-conjugated hydrogels, results in a colorimetric detection of the attached peptides, quantified using absorbance spectroscopy. The presence of the conjugated peptide was represented as the absorbance from each peptide conjugated hydrogel, normalized to the absorbance of the alginate hydrogel alone. A similar level of absorbance was detected for each peptide and ranged from 1.6 to 2.2-fold increase in absorbance as compared to alginate alone, for HAV10 and ADT6 conjugated hydrogel respectively.

hESC Attachment to Peptide Conjugated Alginate Hydrogel.

Having confirmed peptide conjugation to the alginate hydrogel, our first step was to analyze cell attachment to each peptide conjugated substrate. Peptide concentration during conjugation was varied from 0 µg/ml (EDC/NHS activation of alginate alone) to 500 µg/ml. hPSCs were treated with Y-27632 prior to harvesting, and seeded as single cells on the alginate conjugated with HAV10, ADT10, HAV6, and ADT6. As steric hindrance could significantly influence cellular access to the peptide, both a short (6 amino acids) and long (10 amino acids) variant of peptides mimicking the bulge (ADT) and groove (HAV) regions of E-cadherin, were examined. Prior to seeding, cells were labeled using DiD, a lipophilic fluorescent dye, which is incorporated into the cell membrane. After 1 day, cell attachment was quantified for each tested condition using the LI-COR Odyssey scanner. Percent cell attachment was determined by scanning the signal for total seeded cells (prior to wash) and attached cells (post-wash) and normalizing the attached cell MFI to the total cell MFI, for each peptide and peptide concentration (FIG. 9A).

For each peptide, increasing peptide concentration resulted in a corresponding increase in cell attachment. Cell attachment to the HAV10 and ADT6 substrates peaked at the 50 µg/ml condition, after which attachment decreased slightly or was unchanged. Cell attachment to the HAV10 conjugated substrate was essentially unchanged from the control, until a sharp increase in attachment was observed at the 50 µg/ml condition. Cells attached to the ADT10 substrate continuously increased as peptide concentration was increased, and showed the highest cell attachment among all peptides, at all concentrations except 50 µg/ml. Interestingly, while the HAV6 conjugated substrate only showed higher cell attachment than the HAV10 substrate at concentrations less than 100 µg/ml, at the highest concentration of 500 µg/ml it showed higher cell attachment than HAV6 and HAV10 and was on par with ADT10. FIG. 9B shows representative day 1 LIVE/DEAD images of cells attached to alginate conjugated with 50 µg/ml for each peptide. It is important to note that cells were plated as single cells, upon attachment and interaction with the E-cadherin mimicking substrates, they quickly began to form small, rounded colonies when in contact with peptide modified alginate. Thus, hPSCs showed a concentration dependent attachment to peptide modified alginate, and each peptide performed similarly when considering cell attachment. While there was quantitative differences in cell attachment in individual peptides, cell morphology appeared similar in all the tested conditions.

hESC Viability and Expansion Potential after Propagation.

Figure 10:
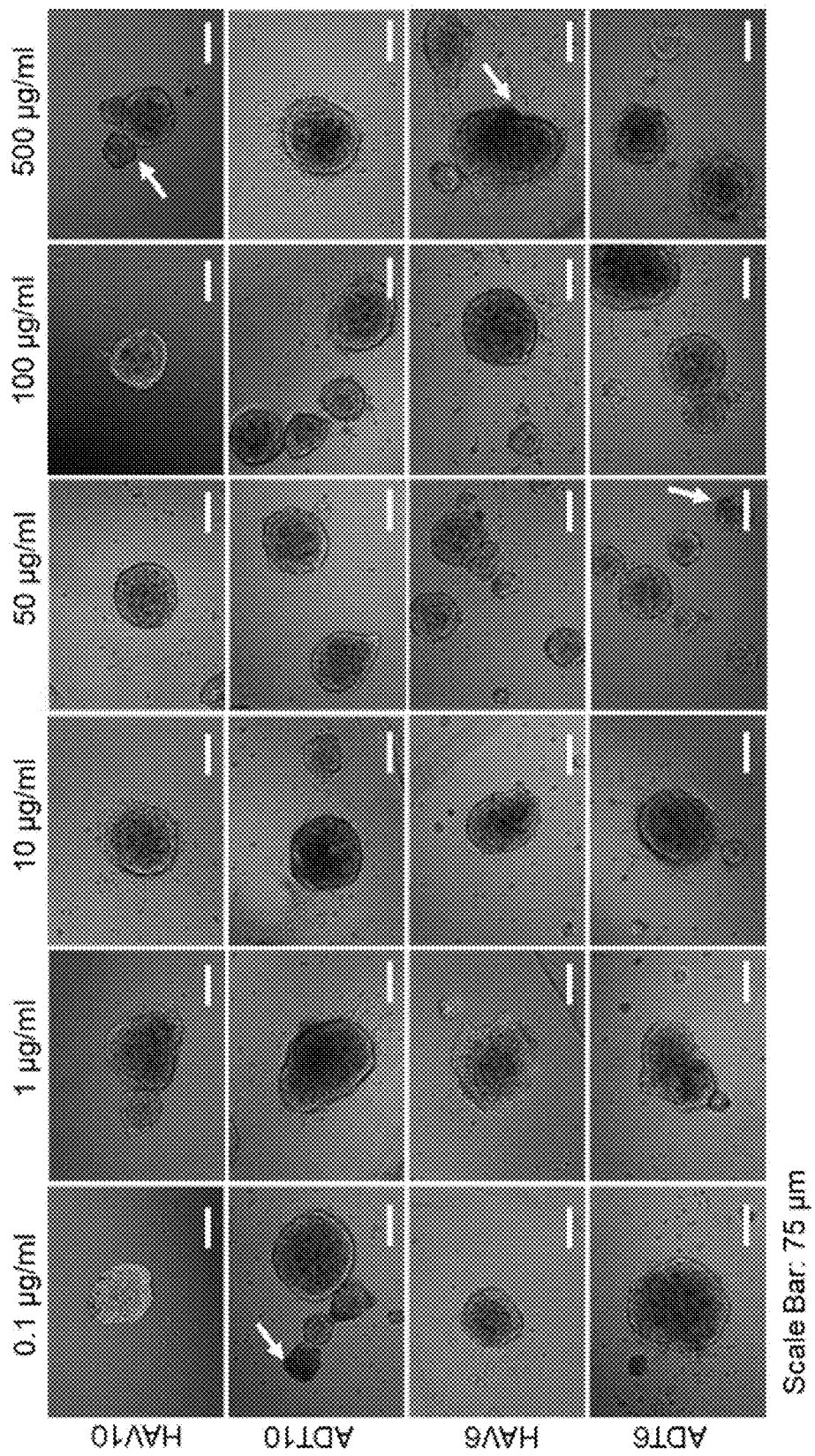
FIG. 10. Cell viability and morphology after 6 days of propagation for each peptide, conjugated at 0-500 µg/ml. White arrows indicate apoptotic single cells observed on the periphery of some colonies after propagation.

Having confirmed and quantified initial cell attachment, we next evaluated the potential of the E-cadherin mimicking substrates to support hPSC propagation. Cell viability and morphology were analyzed after 6 days of propagation using the LIVE/DEAD assay, on each of the peptide modified alginate hydrogels, again conjugated with 0.1-500 µg/ml of each peptide (FIG. 10).

Overall, all the tested peptides exhibited similarly high cell viability without any obvious dependence of viability on peptide concentration. For the most part, apoptotic colonies were not observed after the 6 days of propagation, however a small number of apoptotic cells were observed on the periphery of colonies in some conditions. Additionally, a small population of apoptotic single cells was observed, which appeared to have shed off the colonies during culture, or died initially during the seeding step. For each peptide, at all concentrations tested, the colony size increased during the 6 days propagation period, and retained the characteristic round and uniform hPSC colony morphology. However, the colonies appeared to have slightly "domed" or "pancake"- like morphology, as shown by darker regions in the center of the colony in the microscopy images, indicating that the hPSC colonies were thicker in the center as compared to the edges. While little to no difference in colony size or diameter was observed when comparing across each peptide, colony size did appear to change in response to peptide concentration. For the most part though, larger colonies were observed at the lower peptide concentrations, and as concentration was increased, there appeared to be a higher occurrence of small colonies, although larger colonies were still observed.

Figure 11:
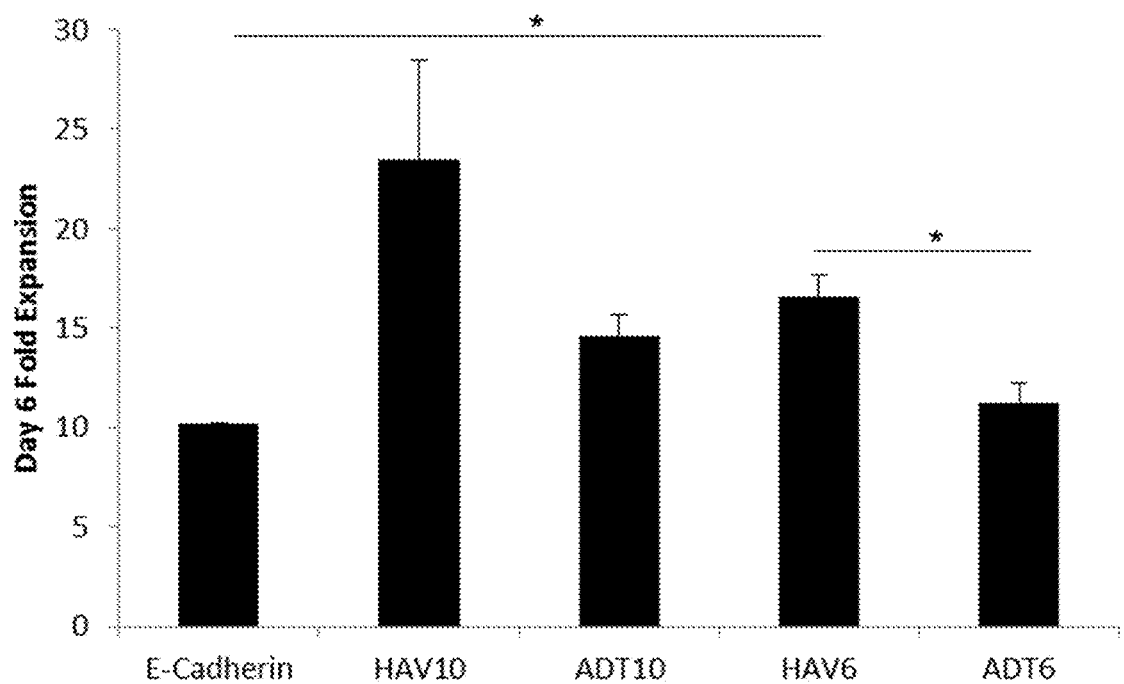
FIG. 11. Day 6 hPSC expansion potential on recombinant e-cadherin, or alginate conjugated with each peptide. n=3, results were considered significant if *P<0.05, **P<0.01.

Since high cell expansion is necessary to generate clinically relevant numbers of hPSCs, we next quantified the expansion potential of hPSCs grown on each peptide. Expansion potential was determined by normalizing cell number after 6 days of propagation, by day 1 cell number using MTS. FIG. 11 shows the fold expansion of hPSCs on alginate modified with 50 µg/ml of each peptide.

The highest expansion was observed with hPSCs grown on HAV10 substrates, showing an approximately 23-fold expansion. Interestingly, while still high, cells propagated on recombinant E-cadherin protein showed only a 10-fold expansion over 6 days of propagation. ADT10 conjugated alginate also showed higher expansion than E-cadherin, with an approximately 14 fold expansion. HAV6 and ADT6 showed a similar trend as the longer peptides, although expansion was lower in magnitude, with a 16 and 11-fold expansion, respectively. Taken together, it is clear that the E-cadherin mimicking substrates can support hPSC proliferation, and high expansion potential.

hESC Pluripotency on Peptide Modified Substrate.

Figure 12:
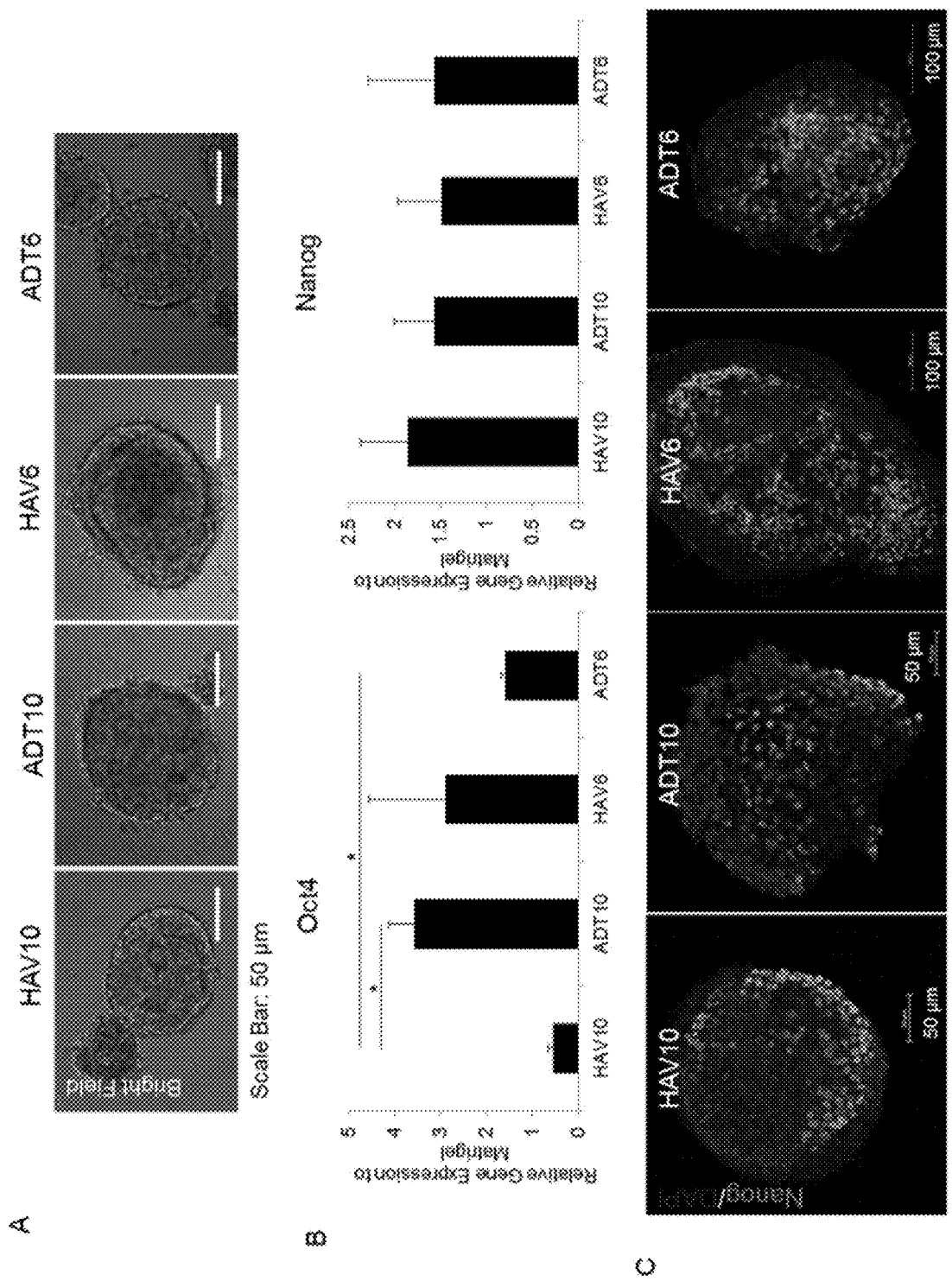
FIG. 12. hPSC pluripotency after propagation on the peptide modified alginate substrate. (A) Phase contrast images of hPSC morphology after 6 days of propagation on alginate modified with 50 µg/ml of HAV10, ADT10, HAV6, or ADT6. (B) Gene expression analysis of OCT4 and Nanog. n=3, results were considered significant if *P<0.05, **P<0.01. (C) Nanog immunostaining of hPSC colonies propagated on each peptide conjugated substrate.

Having confirmed that the substrates supported attachment and propagation of hPSCs, the next step was to analyze the maintenance of hPSC pluripotency after propagation. hPSC pluripotency is the ability to become any cell type in the body, and along with self-renewal, is the defining characteristic of hPSCs. The maintenance of pluripotency is critical for the downstream differentiation of hPSC into any functional cell types, for cell therapy applications. hPSCs were seeded on alginate conjugated with 50 µg/ml of HAV10, ADT10, HAV6, or ADT, and propagated for 6 days. Since cell attachment and propagation did not change considerably when alginate was conjugated with peptide concentrations higher than 50 µg/ml, this condition was chosen to evaluate hPSC pluripotency for each peptide sequences. As before, cell morphology was similar across each peptide, and appeared to have similar morphology to the typical hPSC colony (FIG. 12A).

Pluripotency was first analyzed by qRT-PCR for gene expression of OCT4 and Nanog, and evaluated with respect to cells propagated on Matrigel. As illustrated in FIG. 12B, with the exception of HAV10, cells grown on all the other peptides exhibited stronger expression of OCT4 and NANOG gene expression than in Matrigel. While cells propagated on HAV10 substrates showed an approximately 2-fold down regulation of OCT4 compared to Matrigel controls; the expression of Nanog was slightly upregulated. On the other hand, cells cultured on HAV6 showed a 2 and 1.5 fold upregulation of OCT4 and Nanog, respectively, compared to Matrigel. The ADT10 modified substrate had the highest upregulation of pluripotency markers, with 3 and 1.5-fold upregulation of OCT4 and Nanog respectively, compared to Matrigel. Cells propagated on ADT10 showed significantly higher expression of OCT4, as compared to cells on HAV10. Similarly, ADT6 also retained good pluripotency with expression of OCT4 and Nanog on par with Matrigel, and showed significantly higher OCT4 expression compared to HAV10. Maintenance of pluripotency was further confirmed by protein immunostaining for Nanog (FIG. 6C). Cells positive for Nanog were clearly abundant in hPSC colonies propagated on each of the peptide modified substrates. Thus, it is clear that hESCs grown on each E-cadherin mimicking substrate retained high pluripotency, which were comparable to, and even higher, than the Matrigel control.

hESC Differentiation Potential.

Figure 13:
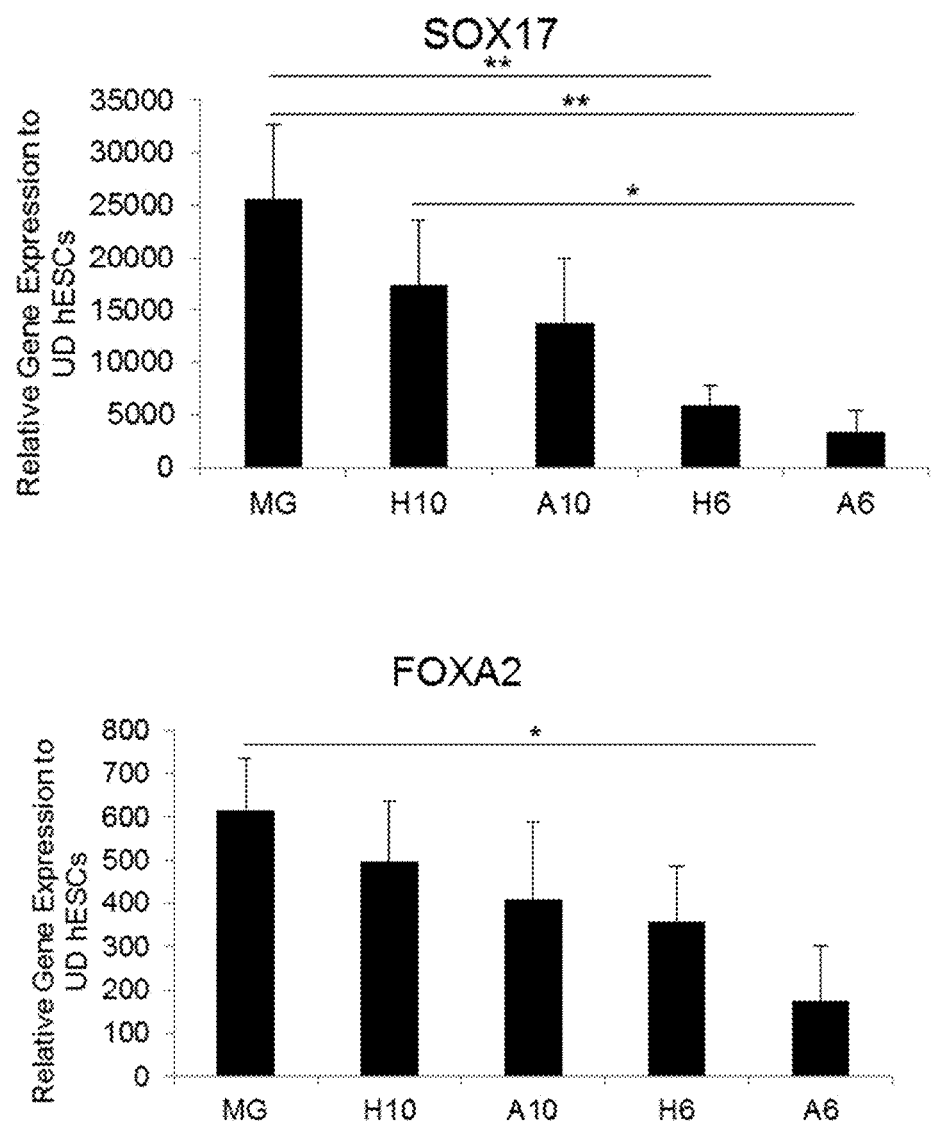
FIG. 13. Differentiation potential of hESCs propagated on e-cadherin peptide mimicking substrates. hPSCs were induced to the definitive endoderm stage using chemical induction. qRT-PCR was used to analyze the relative gene expression of SOX17 and FOXA2 for cell grown on each peptide conjugated hydrogel. n=3, results were considered significant if *P<0.05, **P<0.01.

Having confirmed that hPSCs maintained high pluripotency after being propagated on the E-cadherin mimicking substrates, the next question was if the differentiation potency was also maintained. To evaluate differentiation potential, cells were induced toward the definitive endoderm (DE) germ layer. Differentiation was analyzed after hPSCs were propagated on alginate modified with each of the peptides, and subsequently induced to the DE stage. FIG. 13 shows gene expression analysis of SOX17 after DE induction, which showed a strong upregulation for cells grown on HAV10 (~15000-fold) and ADT10 (~13700-fold), as compared to undifferentiated hESC controls.

Although still highly upregulated, expression of SOX17 on the shorter peptides HAV6 and ADT6 showed an upregulation of 5900 and 3400-fold respectively, compared to undifferentiated controls. While cells grown on the Matrigel controls showed a 25000-fold upregulation of SOX17, cells grown on the HAV10 and ADT10 peptide modified substrates showed no statistically significant difference compared to Matrigel. Likewise, gene expression analysis of FOXA2 showed a similar trend, although of a lower magnitude, with fold increases of 497, 409, 355, and 174 for HAV10, ADT10, HAV6, and ADT6, respectively. Again, however, there was no statistical difference between cells differentiated on Matrigel, as compared to HAV10 or ADT10 based substrates. These findings indicate successful induction of hESC to the DE stage, confirming cells propagated on the peptide modified substrates retained differentiation potency.

Cell Attachment and Pluripotency Using Peptide Combinations.

Figure 14:
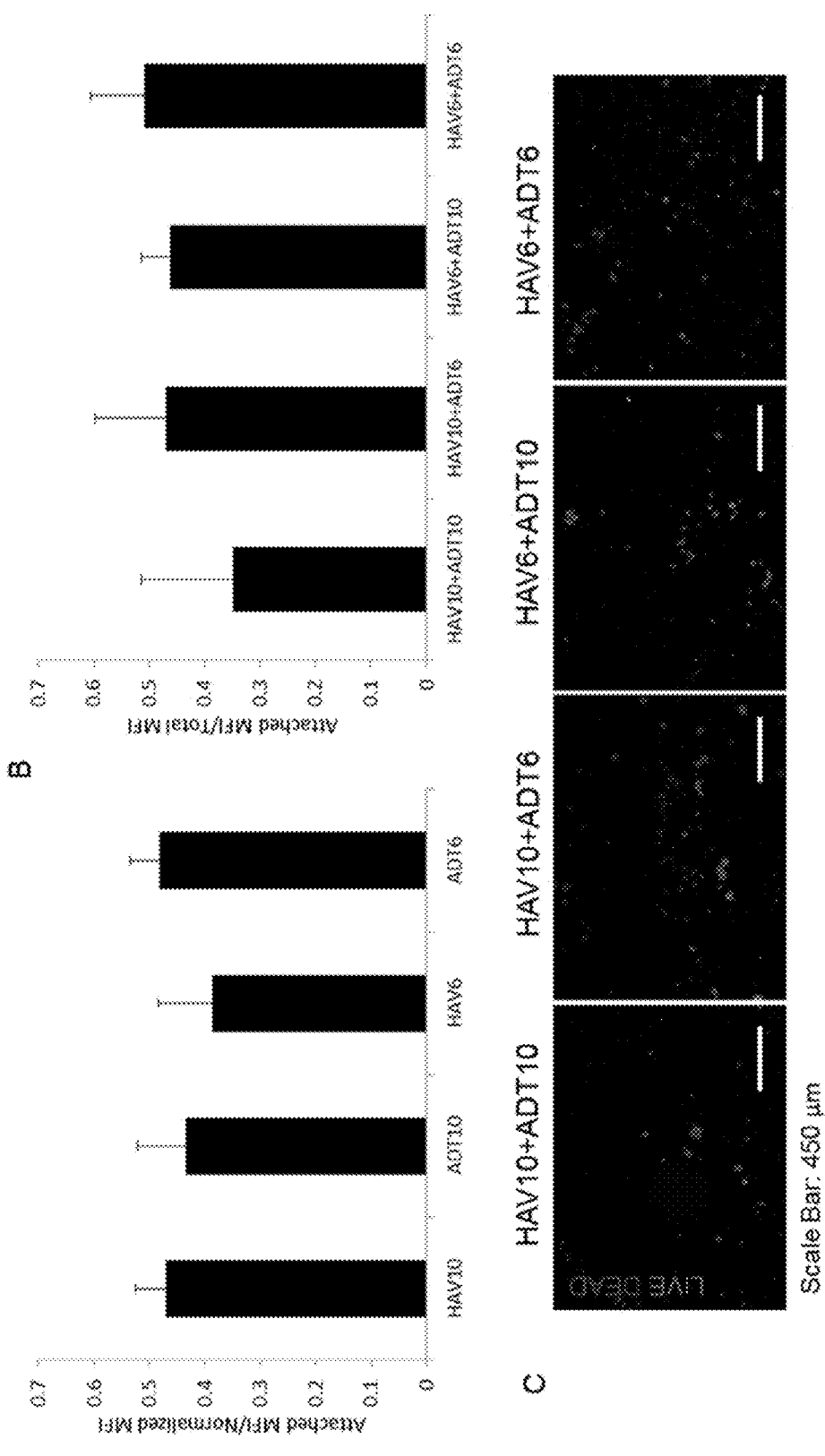
FIG. 14. Day 1 hPSC attachment to alginate modified with combination of HAV and ADT peptides. (A) Day 1 attachment on alginate conjugated with 50 µg/ml of each peptide individually. (B) Day 1 attachment to alginate conjugated with combination of each peptide, each conjugated at 50 µg/ml. (C) Representative LIVE/DEAD images of cell attached to alginate conjugated with peptide combination.

In analysis performed thus far, specific peptide has specific advantages. For example, while ADT10 appeared to support the highest initial cell attachment, and retained the highest pluripotency, HAV10 showed the highest expansion potential and level of differentiation. Hence, we next examined if attachment, viability, and pluripotency further improved by conjugating alginate with a combination of peptides. Thus, Alginate was conjugated with the following peptide combinations: HAV10+ADT10, HAV10+ADT6, ADT10+HAV6, or ADT6+HAV6, using 50 µg/ml for each peptide. Single cell hPSCs were seeded on each substrate, and attachment and cell viability were evaluated after 1 day (FIG. 14).

Both attachment and cell viability for each peptide combination was similar to that seen when individual peptides were conjugated alone. Specifically, cell attachment ranged from 0.38-0.48% attachment for individual peptides, and similarly, cell attachment with peptide combinations ranged from 0.35-0.5%. Thus, conjugation of peptide combination did not significantly alter attachment from single peptides.

Figure 15:
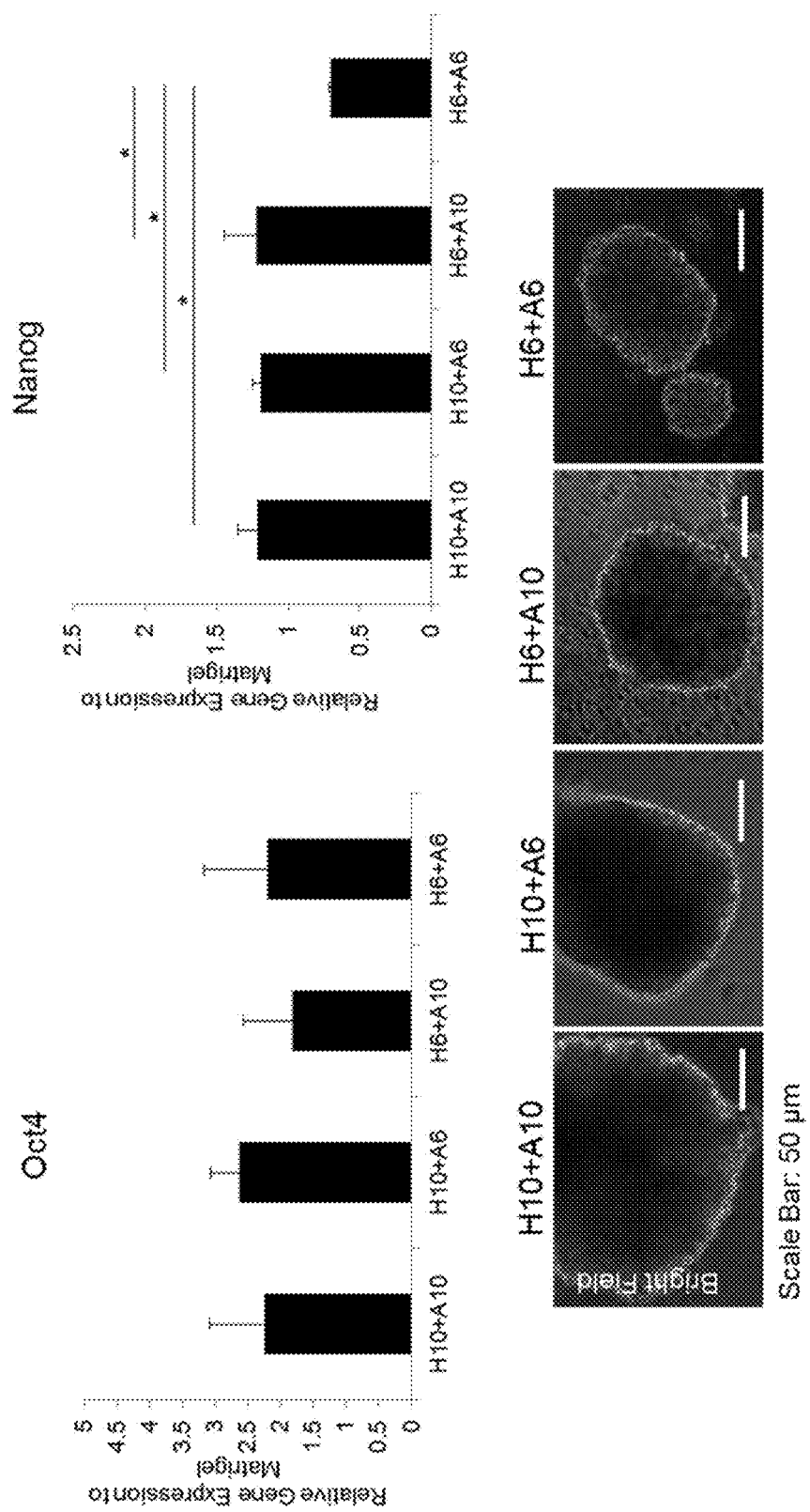
FIG. 15. hPSC pluripotency after propagation on alginate modified with combination of HAV and ADT peptides.
Figure 16:
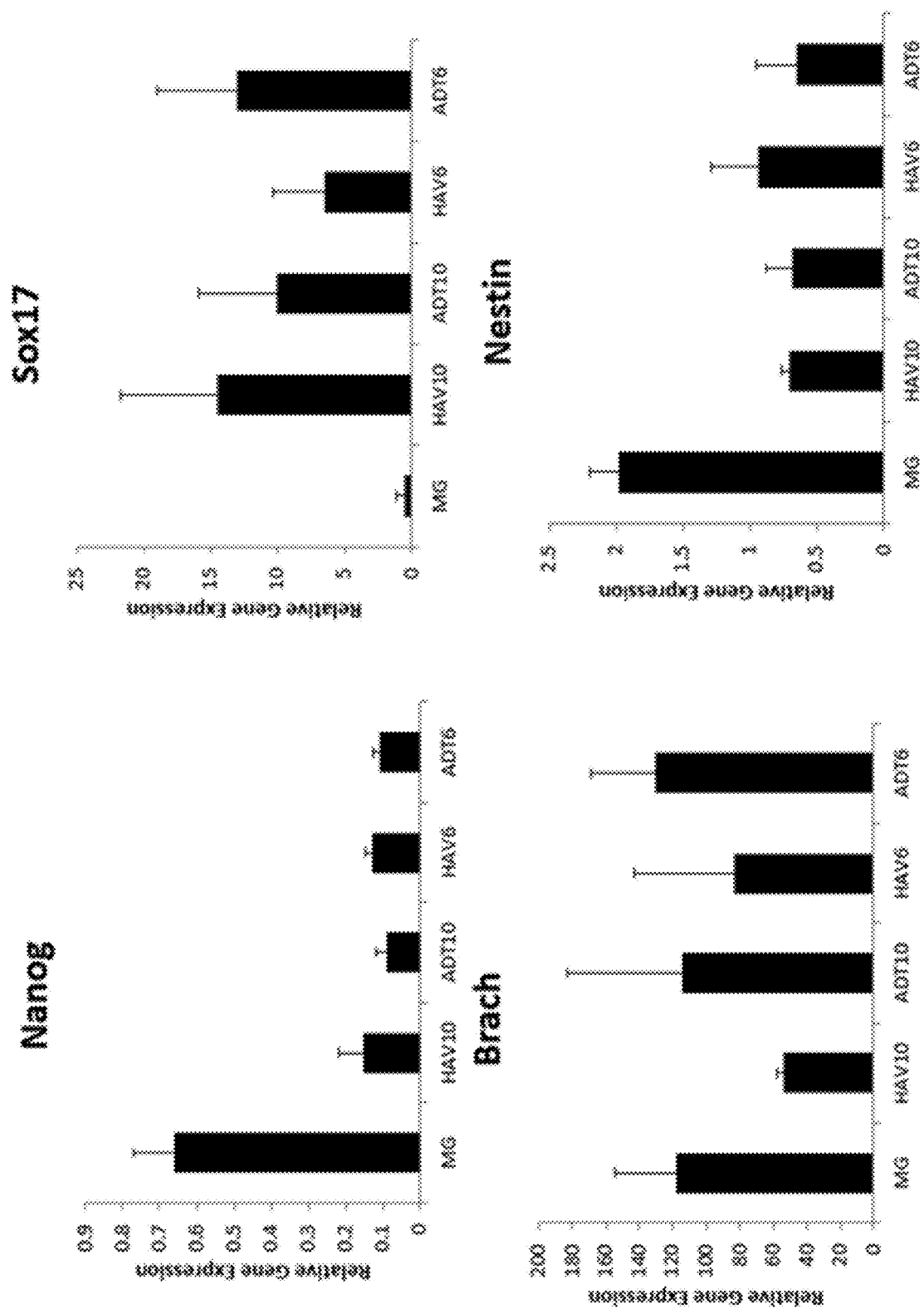
FIG. 16. Provides graphs showing expression of Nanog, Sox17, Brach, and Nestin marker as described in Example 4.

While peptide combinations did not affect cell attachment significantly, it did have an effect on hPSC pluripotency. Previously, we observed that OCT4 expression was down regulated compared to Matrigel on HAV10 substrates, and upregulated on ADT10 substrates. Interestingly, combination of HAV10 and ADT10 resulted in 2-fold upregulation of OCT4 expression compared to Matrigel controls (FIG. 15).

All other peptide combinations showed OCT4 expression to be on par with the Matrigel controls. Similarly, each peptide combination showed Nanog expression to be on par with the Matrigel control, with the exception of the HAV6+ADT6 conditions. When the peptides were combined during conjugation, the resulting Nanog expression was slightly down regulated, while the peptides showed a slight upregulation when conjugated individually. Taken together, while cell attachment was unaffected by combining the peptide, an increase in pluripotency was observed with some combinations.

This example illustrates the feasibility of incorporating synthetic peptides mimicking E-cadherin into a hydrogel substrate for the single cell culture of hPSCs. The use of a low cost synthetic peptide-based substrate for hPSC culture can be used as a direct replacement for current expensive animal derived platforms, such as Matrigel. The use of E-cadherin-based peptides has the potential to mitigate hPSC death occurring when these cells are cultured as single cells. This platform can then be further extended to 3D culture for biomanufacturing of hPSC in the bioreactor setting. Thus, each of the four peptides tested supported single hPSC attachment and viability, maintained hPSC pluripotency, and retained hPSC differentiation potential. Each peptide supported both good initial attachment and viability, as well as hPSC propagation. While hPSCs maintained pluripotency and differentiation potential on the peptide-conjugated substrates, some dependence on peptide length and type was observed.

These findings showed that alginate conjugated with each of the tested peptides supported single hPSC attachment. Cell attachment increased as peptide concentration was increased and was similar for HAV10, ADT10, HAV6, and ADT6 conjugated substrates. This is in contrast to a previous report which found that E-cadherin alone did not support single hPSC attachment and clonal expansion, but required a combination of E-cadherin with ECM, in this case, laminin fragments (Rodin et al., *Clonal culturing of human embryonic stem cells on laminin-521/E-cadherin matrix in defined and xeno-free environment*. Nat Commun. 2014; 5.). Similarly, while not shown with hPSCs, previous work with hMSCs showed that methacrylated hyaluronic acid hydrogels conjugated with a HAV containing N-cadherin peptide supported hMSC attachment, as well as chondrogenesis (Bian et al., *Hydrogels that mimic developmentally relevant matrix and N-cadherin interactions enhance MSC chondrogenesis*. Proc Natl Acad Sci USA. 2013; 110:10117-22) and osteogenesis (Zhu et al., *Hydrogels functionalized with N-cadherin mimetic peptide enhance osteogenesis of hMSCs by emulating the osteogenic niche*. Biomaterials. 2016; 77:44-52.). Again, these substrates engaged cell-cell contacts through the N-cadherin peptide and cellular cadherin's, as well as integrin's through the hyaluronic acid. It is unclear whether the N-cadherin peptide alone was responsible, or if a combination with integrin is necessary. Here, hPSC attachment was observed without additional ECM components, and was dependent on peptide concentration, although only a slight dependence on peptide type and length was observed.

It was then determined if the combined conjugation of peptides from both the bulge and groove region of the EC1 domain of E-cadherin could improve cellular attachment. Results showed that using a combination of HAV and ADT peptides did not result in an increase in cell attachment, as compared to single peptides. These results concur with previous reports, where a combination of peptides from the bulge and groove region did not increase the inhibition of tight intracellular cell-cell junctions on CaCo-2 and MDCK cells, as compared to individual peptide (Sinaga et al., *Increasing paracellular porosity by E-cadherin peptides: discovery of bulge and groove regions in the EC1-domain of E-cadherin*. Pharm Res. 2002; 19:1170-9; Kiptoo et al., *Enhancement of Drug Absorption through the Blood-Brain Barrier and Inhibition of Intercellular Tight Junction Resealing by E-Cadherin Peptides*. Mol Pharmaceut. 2011; 8:239-49.). However, these studies combined the peptides by linking them together, forming a single peptide with bioactive domains from both regions. Here, a combination of single HAV and ADT peptides were conjugated to the alginate substrate. Additionally, the previous studies required the peptides to be in solution, as opposed to being attached to the culture surface. Taken together, the findings, as well as the previous reports, clearly indicate that engaging both the bulge and groove region is not required to invoke a cellular response. Thus, the use of fused HAV-ADT peptides, or a combination of single HAV and ADT peptides, did not enhance peptide performance, as compared to individual HAV or ADT peptides.

E-cadherin peptides supported good initial cell attachment, however supporting long term culture and high cell expansion is also relevant. hPSC expansion potential on the peptide-modified alginate is a prerequisite for evaluating feasibility of these substrates for large scale biomanufacturing goals. Here, we observed that hPSCs propagated for 6 days on our substrate achieved an approximately 15-23-fold expansion, which was comparable to previous studies with material (Bardy et al. *Microcarrier suspension cultures for high-density expansion and differentiation of human pluripotent stem cells to neural progenitor cells*. Tissue Eng Part C Methods. 2013; 19:166-80; Ting et al. *An intermittent rocking platform for integrated expansion and differentiation of human pluripotent stem cells to cardiomyocytes in suspended microcarrier cultures*. Stem Cell Res. 2014; 13:202-13.). Further, the cells propagated on each peptide modified substrate retained high viability. Interestingly, it was observed that hPSC propagated on the full E-cadherin protein supported only a 10-fold expansion. Taken together, these results show that E-cadherin peptide-modified substrates support high cell attachment, proliferation and cell expansion.

While supporting cell attachment is important in evaluating peptide performance, the long term goal is to incorporate these peptides in alginate in the 3D setting, and thus ensuring cell-peptide interaction. The evaluation of pluripotency after propagation on the E-cadherin peptide substrates informs the optimal settings for future 3D platforms. Nagaoka et al. showed that hPSCs passaged and cultured as colonies on human recombinant E-cadherin substrates maintained pluripotency and self-renewal (Nagaoka et al. *Culture of human pluripotent stem cells using completely defined conditions on a recombinant E-cadherin substratum*. Bmc Dev Biol. 2010; 10.). Herein however, the hPSC starting population being plated on peptide-conjugated substrates consisted of single cells and not colonies, which is more advantageous for large scale bioprocessing. Analysis of the pluripotency genes OCT4 and Nanog showed clear differences in peptide performance, which appeared to be dependent on peptide type and length. Specifically, OCT4 and Nanog expression was down regulated 2-fold and upregulated 1.9-fold, respectively, on the HAV10 substrate. However, hPSCs propagated on the ADT10 substrates showed a 3.6 and 1.6-fold upregulation of OCT4 and Nanog, respectively. Interestingly, while no effect was seen on cell attachment, cells propagated on alginate conjugated with a combination of HAV10 and ADT10, showed an OCT4 upregulated by 2.2-fold. Thus, the addition of ADT10 appeared to rescue the pluripotency of hPSCs propagated on HAV10 alone. This indicates that while both the bulge and groove region of E-cadherin was not required for cell attachment, it may be advantageous for maintenance of hPSC pluripotency.

Maintaining pluripotency is essential for large scale bioprocessing and production of clinically relevant cells number; however, the maintenance of good differentiation potential is also required for cell therapy applications. To evaluate the differentiation potential on the E-cadherin peptide modified substrate described herein, we evaluated hPSC germ layer induction to the DE stage after propagation on alginate conjugated with each of the E-cadherin peptides. The DE layer gives rise to a number of functional cell types, such as insulin-producing cells and hepatocytes, all of which are in high demand for cellular therapy. The DE gene markers SOX17 and FOXA2 were highly upregulated on each of the four substrates; however, HAV10 and ADT10-conjugated substrates showed the best performance. The level of differentiation on E-cadherin peptides was comparable to the Matrigel control.

In conclusion, short, inexpensive, synthetic peptides derived from E-cadherin can be used in place of the full E-cadherin protein to propagate hPSCs. Peptide-modified alginate substrates supported good initial cell attachment, viability after propagation, and the cells demonstrated an expansion potential on par with recombinant E-cadherin. More importantly, however, hPSCs cultured on this substrate maintained high pluripotency and differentiation potential.

Example 4. Pluripotency of hESCs Culture on Peptides of Table 1

Undifferentiated hESCs were seeded onto alginate hydrogels conjugated with each peptide (50 µg/ml), and propagated for 6 days in mTSeR1 (culture media which maintains pluripotent state). Cells were then exposed to DMEM+20% FBS for 7 days, to allow for spontaneous differentiation in the absence of factors which maintain pluripotency. Spontaneous differentiation was analyzed by gene expression using qRT-PCR for a pluripotency marker (Nanog), and genes representing expression of cells from each germ layer. SOX17, Brachyury, and Nestin were analyzed for specification to the endoderm, mesoderm, and ectoderm germ layers, respectively. As shown in FIG. 14, a decrease in Nanog expression coincides with a loss of pluripotency as cell undergo differentiation. Upregulation of each germ layer marker indicates the hESCs retained the pluripotency (ability to differentiate to all cell types in the body) characteristic prior to initiation of spontaneous differentiation. Additionally, this also indicates the hPSC propagated on the peptide modified alginate substrates retained their differentiation potential.

The following clauses provide examples of various aspects of the present invention:

1. A composition for use in propagating pluripotent stem cells from single cells, comprising a biocompatible hydrogel, optionally a synthetic or naturally derived polysaccharide hydrogel, linked to a polypeptide comprising a cell-binding sequence of an epithelial cadherin, optionally human epithelial cadherin, extracellular domain.
2. The composition of clause 1, wherein the hydrogel is a synthetic or naturally-derived polysaccharide hydrogel.
3. The composition of clause 1, wherein the polypeptide ranges from 5 to 100, from five to 75, from five to 50, from five to 25, from five to 20, from five to 15, from five to ten, or from six to ten amino acids in length.
4. The composition of clause 2, wherein the polysaccharide is a carboxylated polysaccharide.
5. The composition of any one of clauses 2-4, wherein the biocompatible polysaccharide hydrogel is alginate.
6. The composition of any one of clauses 1-5, wherein the polypeptide comprises:
   a. the sequence LFSHAVSSNG (SEQ ID NO: 2), SHAVSS (SEQ ID NO: 3), QGADTPPVGV (SEQ ID NO: 4), and/or ADTPPV (SEQ ID NO: 5);
   b. a sequence comprising the amino acid sequence HAV and/or ADT;
   c. a sequence having at least five consecutive amino acids of SHAVSS (SEQ ID NO: 3) and/or ADTPPV (SEQ ID NO: 5); or
   d. a sequence having at least 80% sequence identity with SHAVSS (SEQ ID NO: 3) and ADTPPV (SEQ ID NO: 5).
7. The composition of clause 6, wherein the polypeptide ranges from six to ten amino acids in length.
8. The composition of any one of clauses 1-7, wherein the polypeptide is chosen from:

```
                                    (HAV10, SEQ ID NO: 2)
    LFSHAVSSNG;

(HAV6, SEQ ID NO: 3)
    SHAVSS;

(ADT10, SEQ ID NO: 4)
    QGADTPPVGV,
    and (ADT6, SEQ ID NO: 5)
    ADTPPV.
```

9. The composition of any one of clauses 1-8, wherein the polypeptide is linked directly to the hydrogel by an amide bond.
10. The composition of any one of clauses 1-9, comprising free carboxyl groups.
11. The composition of clause 10, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of monomers of the hydrogels, or, when present, saccharide moieties of the polysaccharide, have the peptide linked thereto.
12. The composition of any one of clauses 1-11, wherein the composition is anionic and is in the form of capsules formed with a divalent cation, such as barium or calcium, optionally with 15 mM or less barium added in the form of an inorganic salt, for example as barium chloride.
13. A method of propagating pluripotent stem cells, comprising:
   a. depositing one or more pluripotent stem cells onto a composition according to any one of clauses 1-12; and
   b. culturing the deposited pluripotent stem cells in a cell culture.
14. The method of clause 13, wherein the pluripotent stem cells are embryonic stem cells.

15. The method of clause 13, wherein the pluripotent stem cells are induced pluripotent stem cells.
16. The method of any one of clauses 13-15, wherein the pluripotent stem cells are human.
17. The method of any one of clauses 13-16, wherein the cells are cultured in a layer on a substrate.
18. The method of any one of clauses 13-16, wherein the cells are cultured in suspension, optionally wherein the suspension culture is agitated (e.g., stirred or shaken).
19. The method of any one of clauses 13-16, wherein the cells are cultured in a bioreactor, optionally where cell culture media flows through the bioreactor from a source of the media.
20. The method of any one of clauses 13-19, further comprising culturing the cells in the presence of a ROCK inhibitor, followed by culturing the cells in medium without the ROCK inhibitor to allow for colony formation, wherein the ROCK inhibitor is optionally Y-27632.
21. A method of making a composition supportive of pluripotent cell expansion, comprising conjugating (covalently attaching) a polypeptide comprising a cell-binding sequence of an epithelial cadherin, such as human epithelial cadherin, extracellular domain to a biocompatible hydrogel, optionally to a synthetic or naturally derived polysaccharide hydrogel.
22. The method of clause 21, wherein the hydrogel is a polysaccharide hydrogel.
23. The method of clause 22, wherein the polysaccharide is a carboxylated polysaccharide.
24. The method of any one of clauses 21-23, wherein the biocompatible polysaccharide hydrogel is alginate.
25. The method of clause 21, wherein the polypeptide ranges from 5 to 100, from five to 75, from five to 50, from five to 25, from five to 20, from five to 15, from five to ten, or from six to ten amino acids in length.
26. The method of any one of clauses 21-25, wherein the polypeptide comprising a cell-binding sequence of an epithelial cadherin extracellular domain comprising:
    the sequence LFSHAVSSNG (SEQ ID NO: 2), SHAVSS (SEQ ID NO: 3), QGADTPPVGV (SEQ ID NO: 4), and/or ADTPPV (SEQ ID NO: 5);
    a sequence comprising the amino acid sequence HAV and/or ADT;
    a sequence having at least five consecutive amino acids of SHAVSS (SEQ ID NO: 3) and/or ADTPPV (SEQ ID NO: 5); or
    a sequence having at least 80% sequence identity with SHAVSS (SEQ ID NO: 3) and ADTPPV (SEQ ID NO: 5).
27. The method of clause 26, wherein the polypeptide ranges from six to ten amino acids in length.
28. The method of any one of clauses 21-26, wherein the polypeptide is chosen from:

```
                     (HAV10, SEQ ID NO: 2)
    LFSHAVSSNG;

(HAV6, SEQ ID NO: 3)
    SHAVSS;

(ADT10, SEQ ID NO: 4)
    QGADTPPVGV,
    and (ADT6, SEQ ID NO: 5)
    ADTPPV.
```

29. The method of any one of clauses 21-27, wherein the polypeptide is linked directly to the hydrogel by an amide bond.
30. The method of any one of clauses 21-27, wherein the hydrogel is a polysaccharide and the composition comprises free carboxyl groups.
31. The method of clause 30, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties of the polysaccharide have the peptide linked thereto.
32. The method of any one of clauses 21-30, wherein the hydrogel is an anionic polysaccharide and the composition is in the form of capsules formed with a divalent cation such as an inorganic salt of a divalent cation, such as barium or calcium, optionally with 15 mM or less barium, for example as barium chloride.
33. A method of preparing a cell growth composition, comprising:
    conjugating a polypeptide comprising a cell-binding sequence of an epithelial cadherin, such as human epithelial cadherin, extracellular domain with a polysaccharide, such as a carboxylated polysaccharide, to produce a polypeptide-conjugated polysaccharide;
    mixing pluripotent stem cells with the polypeptide-conjugated polysaccharide; and
    optionally culturing the cells in cell culture medium, such as stem cell medium, optionally exposing the cells in culture to a ROCK inhibitor, such as Y-27632, within the first 1, 2, 3, or 4, days of culture, thereby expanding the cells, wherein when the cells are pluripotent, the cells retain their pluripotency.
34. The method of clause 33, wherein the polypeptide-conjugated polysaccharide is anionic and further comprising exposing the cells mixed with the polypeptide-conjugated polysaccharide to a solution of a divalent cation, such as an inorganic salt of a divalent cation, such as barium or calcium ions, e.g. a salt, such as a calcium chloride or barium chloride, optionally less than or equal to 15 mM of the divalent cation, to produce encapsulated cells
35. The method of clause 33 or 34, wherein the polysaccharide is a carboxylated polysaccharide.
36. The method of any one of clauses 33-35, wherein the biocompatible polysaccharide hydrogel is alginate.
37. The method of any one of clauses 33-36, wherein the polypeptide ranges from 5 to 100, from five to 75, from five to 50, from five to 25, from five to 20, from five to 15, from five to ten, or from six to ten amino acids in length.
38. The method of any one of clauses 33-37, wherein the polypeptide comprising a cell-binding sequence of an epithelial cadherin extracellular domain comprising:
    the sequence LFSHAVSSNG (SEQ ID NO: 2), SHAVSS (SEQ ID NO: 3), QGADTPPVGV (SEQ ID NO: 4), and/or ADTPPV (SEQ ID NO: 5);
    a sequence comprising the amino acid sequence HAV and/or ADT;
    a sequence having at least five consecutive amino acids of SHAVSS (SEQ ID NO: 3) and/or ADTPPV (SEQ ID NO: 5); or
    a sequence having at least 80% sequence identity with SHAVSS (SEQ ID NO: 3) and ADTPPV (SEQ ID NO: 5).
39. The method of clause 38, wherein the polypeptide ranges from six to ten amino acids in length.

40. The method of any one of clauses 33-39, wherein the polypeptide is chosen from:

```
                         (HAV10, SEQ ID NO: 2)
    LFSHAVSSNG;

(HAV6, SEQ ID NO: 3)
    SHAVSS;

(ADT10, SEQ ID NO: 4)
    QGADTPPVGV,
    and (ADT6, SEQ ID NO: 5)
    ADTPPV.
```

41. The method of any one of clauses 33-40, wherein the polypeptide is linked directly to the polysaccharide by an amide bond.
42. The method of any one of clauses 33-41, wherein the polypeptide-conjugated polysaccharide comprises free carboxyl groups.
43. The method of clause 42, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties of the polysaccharide have the peptide linked thereto.
44. A device, comprising a substrate, a first intermediate layer over at least a portion of the substrate comprising a first anionic polysaccharide layer over at least a portion of the substrate and a cationic polyamine layer over at least a portion of the anionic layer, and a second anionic polysaccharide layer over at least a portion of the cationic polyamine layer, wherein the polysaccharide of the first and/or second anionic polysaccharide layer is linked to a polypeptide comprising a cell-binding sequence of an E-cadherin extracellular domain.
45. The device of clause 44, wherein the cationic polyamine comprises a poly(allylamine), for example (poly(allylamine hydrochloride).
46. The device of clause 44, further comprising one or more additional intermediate layers over at least a portion of the first intermediate layer and under the second anionic polysaccharide layer, the one or more additional layers comprising a first anionic polysaccharide layer and a cationic polyamine layer over at least a portion of the anionic layer.
47. The device of any one of clauses 44-46, wherein the polypeptide comprising a cell-binding sequence of an epithelial cadherin extracellular domain comprising:
    the sequence LFSHAVSSNG (SEQ ID NO: 2), SHAVSS (SEQ ID NO: 3), QGADTPPVGV (SEQ ID NO: 4), and/or ADTPPV (SEQ ID NO: 5);
    a sequence comprising the amino acid sequence HAV and/or ADT;
    a sequence having at least five consecutive amino acids of SHAVSS (SEQ ID NO: 3) and/or ADTPPV (SEQ ID NO: 5); or
    a sequence having at least 80% sequence identity with SHAVSS (SEQ ID NO: 3) and ADTPPV (SEQ ID NO: 5).
48. The device of clause 47, wherein the polypeptide ranges from six to ten amino acids in length.
49. The device of any one of clauses 44-48, wherein the polypeptide is chosen from:

```
                         (HAV10, SEQ ID NO: 2)
    LFSHAVSSNG;

(HAV6, SEQ ID NO: 3)
    SHAVSS;

(ADT10, SEQ ID NO: 4)
    QGADTPPVGV,
    and (ADT6, SEQ ID NO: 5)
    ADTPPV.
```

50. The device of any one of clauses 44-49, wherein the polypeptide is linked directly to the polysaccharide by an amide bond.
51. The device of any one of clauses 44-50, wherein the polypeptide-conjugated polysaccharide comprises free carboxyl groups.
52. The device of clause 44, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties of the polysaccharide have the peptide linked thereto.
53. The device of any of clauses 44-52, wherein the composition comprises five or more distinct layers of alginate-poly (allylamine).
54. The device of any of clauses 44-53, wherein the composition further comprises a polyalkylenimine, such as a polyethylenimine layer over at least a portion of the substrate and between the substrate and the first intermediate layer.
55. The device of any of clauses 44-54, wherein the substrate is a bead, a fiber, a tube, or a planar surface.
56. A method of preparing a multi-layered composition for use in propagating pluripotent stem cells from single cells, comprising:
    forming an intermediate layer by forming a first anionic layer over a substrate by depositing a biocompatible natural or synthetic anionic polysaccharide over at least a portion of the substrate and forming a first cationic layer by depositing a polyamine, such as poly(allylamine), such as a poly(allylamine hydrochloride) over at least a portion of the first anionic layer; and
    forming a second anionic layer over the substrate by depositing a biocompatible natural or synthetic anionic polysaccharide over at least a portion of the first cationic layer,
    wherein the polysaccharide of either or both of the intermediate layer or the second anionic layer is covalently linked to a polypeptide comprising a cell-binding sequence of an E-cadherin extracellular domain prior to or after depositing the polysaccharide over the substrate.
57. The method of clause 56, comprising, in order:
    immersing a substrate in a solution of a biocompatible natural or synthetic polysaccharide to form the first anionic layer;

immersing the substrate in a solution of a polyamine, such as poly(allylamine), such as a poly(allylamine hydrochloride) solution to form the first cationic layer; and immersing the substrate in a solution of a biocompatible natural or synthetic polysaccharide to form the second anionic layer.

58. The method of clause 56, further comprising, prior to forming the second anionic layer on the intermediate layer, forming one or more intermediate layers over at least a portion of the first intermediate layer by depositing a biocompatible natural or synthetic polysaccharide over at least a portion of the first intermediate layer and depositing a polyamine, such as poly(allylamine), such as a poly(allylamine hydrochloride) over at least a portion of the polysaccharide of each additional intermediate layer.

59. The method of clause 58, comprising forming at least four additional intermediate layers over the substrate.

60. The method of clause 56, wherein the substrate is washed with a solution comprising sodium chloride after forming each layer.

61. The method of any one of clauses 56-60, wherein the polysaccharide of one or more of the intermediate layers and/or the second anionic layer is a carboxylated polysaccharide.

62. The method of any one of clauses 56-60, wherein the biocompatible polysaccharide hydrogel is alginate.

63. The method of any one of clauses 56-62, wherein the polypeptide ranges from 5 to 100, from five to 75, from five to 50, from five to 25, from five to 20, from five to 15, from five to ten, or from six to ten amino acids in length.

64. The method of any one of clauses 56-63, wherein the polypeptide comprising a cell-binding sequence of an epithelial cadherin extracellular domain comprising:
the sequence LFSHAVSSNG (SEQ ID NO: 2), SHAVSS (SEQ ID NO: 3), QGADTPPVGV (SEQ ID NO: 4), and/or ADTPPV (SEQ ID NO: 5);
a sequence comprising the amino acid sequence HAV and/or ADT;
a sequence having at least five consecutive amino acids of SHAVSS (SEQ ID NO: 3) and/or ADTPPV (SEQ ID NO: 5); or
a sequence having at least 80% sequence identity with SHAVSS (SEQ ID NO: 3) and ADTPPV (SEQ ID NO: 5).

65. The method of clause 63, wherein the polypeptide ranges from six to ten amino acids in length.

66. The method of any one of clauses 56-63, wherein the polypeptide is chosen from:

```
                                     (HAV10, SEQ ID NO: 2)
    LFSHAVSSNG;
                                     (HAV6, SEQ ID NO: 3)
    SHAVSS;
                                     (ADT10, SEQ ID NO: 4)
    QGADTPPVGV,
    and
                                     (ADT6, SEQ ID NO: 5)
    ADTPPV.
```

67. The method of any one of clauses 56-66, wherein the polypeptide is linked directly to the polysaccharide by an amide bond.

68. The method of any one of clauses 56-67, wherein the polypeptide-conjugated polysaccharide comprises free carboxyl groups.

69. The method of clause 68, wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties of the polysaccharide have the peptide linked thereto.

70. The method of any of clauses 56-67, wherein the polysaccharide of either or both of the intermediate layer or the second anionic layer is covalently linked to a polypeptide comprising a cell-binding sequence of an E-cadherin extracellular domain prior to depositing the polysaccharide over the substrate.

71. The method of any of clauses 56-67, wherein the polysaccharide of either or both of the intermediate layer or the second anionic layer is covalently linked to a polypeptide comprising a cell-binding sequence of an E-cadherin extracellular domain after depositing the polysaccharide over the substrate.

72. The method of any one of clauses 56-71, wherein the polypeptide is linked to the polysaccharide by carbodiimide chemistry.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

We claim:

1. A composition for use in propagating human pluripotent stem cells from single human pluripotent cells, comprising a biocompatible, cross-linked, synthetic or naturally derived polysaccharide hydrogel linked to a polypeptide comprising a cell-binding sequence of an epithelial cadherin extracellular domain,
   wherein the cell-binding sequence is at least one of LFSHAVSSNG (HAV10, SEQ ID NO: 2); SHAVSS (HAV6, SEQ ID NO: 3); QGADTPPVGV (ADT10, SEQ ID NO: 4), and ADTPPV (ADT6, SEQ ID NO: 5),
   wherein the composition supports or provides an 11-fold to 23-fold increase in human pluripotent stem cell propagation compared to a control without the cell-binding sequence, and
   wherein the polypeptide is linked directly to the hydrogel by an amide bond.

2. The composition of claim 1, wherein the polysaccharide is a carboxylated polysaccharide.

3. The composition of claim 1, wherein the biocompatible polysaccharide hydrogel is alginate.

4. The composition of claim 1, wherein the cell-binding sequence comprises a sequence having at least five consecutive amino acids of SHAVSS (SEQ ID NO: 3) and/or ADTPPV (SEQ ID NO: 5).

5. The composition of claim 1, wherein the polysaccharide comprises pendant free carboxyl groups, and wherein 99% or less, 95% or less, 90% or less, 80% or less, 75% or less, 70% or less, 60% or less, 50% or less, 40% or less, 30% or less, 25% or less, 20% or less, 10% or less, 5% or less, or 1% or less of saccharide moieties of the polysaccharide, have the polypeptide linked thereto.

6. The composition of claim 1, wherein the composition is anionic and is in the form of capsules formed with a divalent cation.

7. A method of propagating pluripotent stem cells, comprising:
   depositing one or more pluripotent stem cells onto a composition according to claim 1; and
   culturing the deposited pluripotent stem cells in a cell culture.

8. The method of claim 7, wherein the pluripotent stem cells are embryonic stem cells.

9. The method of claim 7, wherein the pluripotent stem cells are induced pluripotent stem cells.

10. The method of claim 7, wherein the pluripotent stem cells are human.

11. The method of claim 7, further comprising culturing the cells in the presence of a ROCK inhibitor, followed by culturing the cells in medium without the ROCK inhibitor to allow for colony formation.

12. The composition of claim 1, wherein the hydrogel is a two-dimensional alginate hydrogel, and wherein the hydrogel is surface-modified with a polypeptide having the sequence of SEQ ID NO: 2.

* * * * *

SEQUENCE LISTING

```
<160> NUMBER OF SEQ ID NOS: 5

<210> SEQ ID NO 1
<211> LENGTH: 882
<212> TYPE: PRT
<213> ORGANISM: Homo sapiens

<400> SEQUENCE: 1

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45
```

```
Gly Arg Val Leu Gly Arg Val Asn Phe Glu Asp Cys Thr Gly Arg Gln
 50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
                 85                  90                  95

His Phe Leu Val Tyr Ala Trp Asp Ser Thr Tyr Arg Lys Phe Ser Thr
                100                 105                 110

Lys Val Thr Leu Asn Thr Val Gly His His Arg Pro Pro His
                115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
                180                 185                 190

Thr Gly Gln Gly Ala Asp Thr Pro Pro Val Gly Val Phe Ile Ile Glu
                195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
                260                 265                 270

Glu Gly Ala Leu Pro Gly Thr Ser Val Met Glu Val Thr Ala Thr Asp
                275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
                340                 345                 350

Glu Gly Leu Ser Thr Thr Ala Thr Ala Val Ile Thr Val Thr Asp Thr
                355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
                420                 425                 430

Asp Gly Ile Leu Lys Thr Ala Lys Gly Leu Asp Phe Glu Ala Lys Gln
                435                 440                 445

Gln Tyr Ile Leu His Val Ala Val Thr Asn Val Val Pro Phe Glu Val
    450                 455                 460
```

```
Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
        690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
                740                 745                 750

Tyr Tyr Tyr Asp Glu Glu Gly Gly Glu Glu Asp Gln Asp Phe Asp
                755                 760                 765

Leu Ser Gln Leu His Arg Gly Leu Asp Ala Arg Pro Glu Val Thr Arg
        770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp
```

```
<210> SEQ ID NO 2
<211> LENGTH: 10
<212> TYPE: PRT
<213> ORGANISM: Artificial Sequence
<220> FEATURE:
<223> OTHER INFORMATION: 10-mer fragment of human e-cadherin

<400> SEQUENCE: 2

Leu Phe Ser His Ala Val Ser Ser Asn Gly
1               5                   10

<210> SEQ ID NO 3
<211> LENGTH: 6
<212> TYPE: PRT
<213> ORGANISM: Artificial Sequence
<220> FEATURE:
<223> OTHER INFORMATION: 6-mer fragment of human e-cadherin

<400> SEQUENCE: 3

Ser His Ala Val Ser Ser
1               5

<210> SEQ ID NO 4
<211> LENGTH: 10
<212> TYPE: PRT
<213> ORGANISM: Artificial Sequence
<220> FEATURE:
<223> OTHER INFORMATION: 10-mer fragment of human e-cadherin

<400> SEQUENCE: 4

Gln Gly Ala Asp Thr Pro Pro Val Gly Val
1               5                   10

<210> SEQ ID NO 5
<211> LENGTH: 6
<212> TYPE: PRT
<213> ORGANISM: Artificial Sequence
<220> FEATURE:
<223> OTHER INFORMATION: 6-mer fragment of human e-cadherin

<400> SEQUENCE: 5

Ala Asp Thr Pro Pro Val
1               5
```